United States Patent
Lee et al.

(10) Patent No.: US 10,414,736 B2
(45) Date of Patent: Sep. 17, 2019

(54) METHOD OF PREPARING EZETIMIBE AND INTERMEDIATE THEREOF

(71) Applicant: Kangwon National University, University Industry Cooperation Foundation, Chuncheon, Gangwon Province (KR)

(72) Inventors: Phil Ho Lee, Chuncheon-si (KR); Koo Yeon Lee, Chuncheon-si (KR); Yonghyeon Baek, Chuncheon-si (KR); Kyusik Um, Chuncheon-si (KR); Byeong Su Kim, Chuncheon-si (KR)

(73) Assignee: Kangwon National University Industry Cooperation Foundation, Gangwon-do (KR)

( * ) Notice: Subject to any disclaimer, the term of this patent is extended or adjusted under 35 U.S.C. 154(b) by 0 days.

(21) Appl. No.: 16/146,129

(22) Filed: Sep. 28, 2018

(65) Prior Publication Data

US 2019/0256479 A1 Aug. 22, 2019

(30) Foreign Application Priority Data

Feb. 21, 2018 (KR) .......................... 10-2018-0020490

(51) Int. Cl.
*C07D 263/26* (2006.01)
*C07D 205/08* (2006.01)
*B01J 31/38* (2006.01)
*B01J 31/22* (2006.01)

(52) U.S. Cl.
CPC ........ *C07D 263/26* (2013.01); *B01J 31/2278* (2013.01); *B01J 31/38* (2013.01); *C07D 205/08* (2013.01); *B01J 2231/543* (2013.01); *C07B 2200/07* (2013.01)

(58) Field of Classification Search
CPC ....... C07D 263/26; C07D 205/08; B01J 31/38
See application file for complete search history.

(56) References Cited

U.S. PATENT DOCUMENTS

2011/0183956 A1* 7/2011 Mravljak ................ C07C 51/09
514/210.02

FOREIGN PATENT DOCUMENTS

| KR | 10-1156588 B1 | 6/2012 |
| KR | 10-1491007 B1 | 2/2015 |
| KR | 2016-0116933 A | 10/2016 |

OTHER PUBLICATIONS

M. Humpl et al., "Stereoselective Synthesis of Ezetimibe via Cross-Metathesis of Homoallylalcohols and α-Methylidene-β-Lactams" J. Org. Chem, 2016, 81 (17), pp. 7692-7699.

* cited by examiner

*Primary Examiner* — Sun Jae Yoo
(74) *Attorney, Agent, or Firm* — Harness, Dickey & Pierce, P.L.C.

(57) ABSTRACT

Disclosed is a method of preparing ezetimibe, including cross-metathesis using a Grubbs $2^{nd}$ catalyst and deprotection using a Pearlman's catalyst, and an intermediate thereof. The method of preparing ezetimibe is useful as an efficient ezetimibe synthesis technique in pharmaceutical fields using ezetimibe as a raw material.

9 Claims, 21 Drawing Sheets

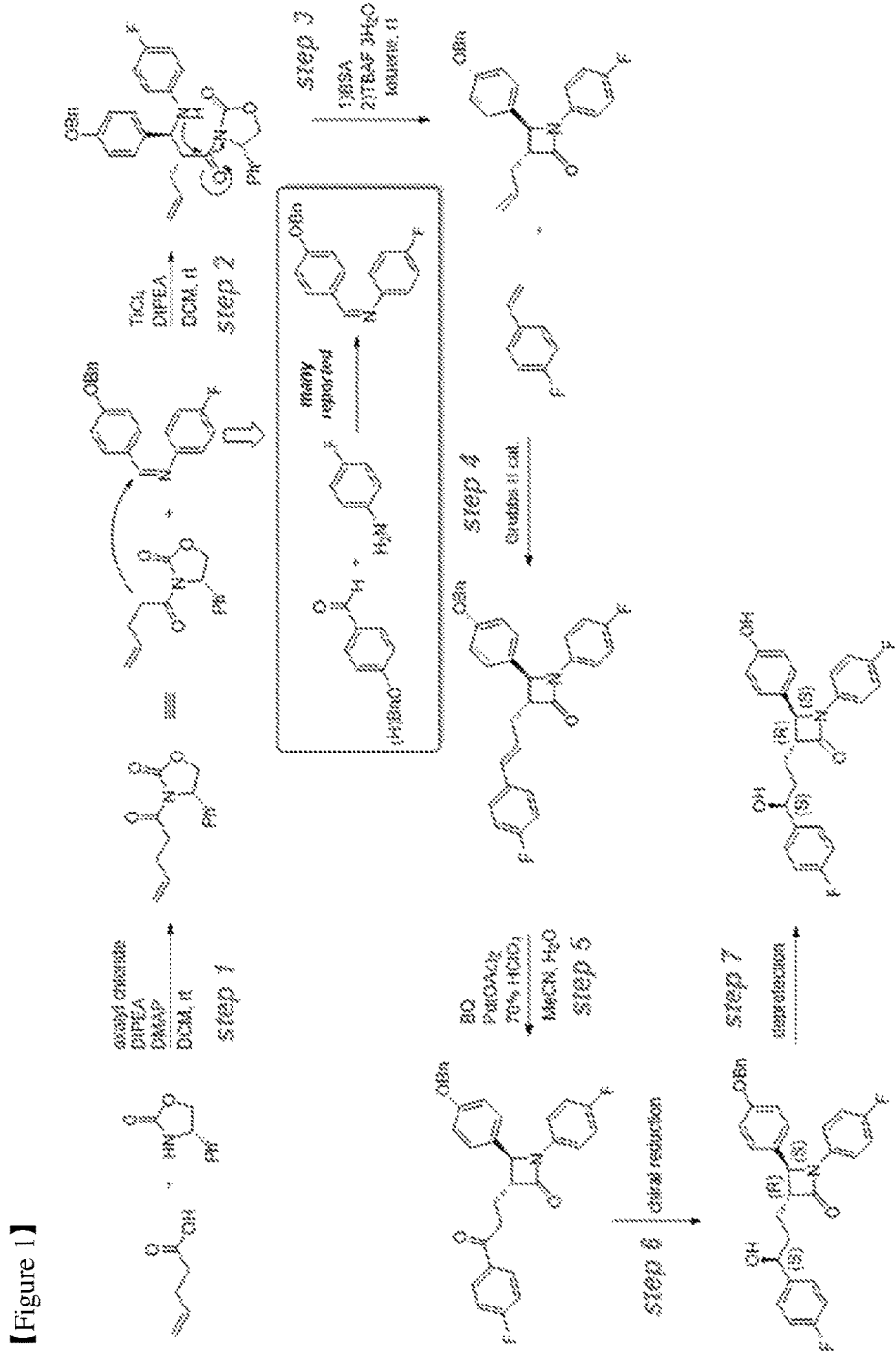
[Figure 1]

[Figure 2]
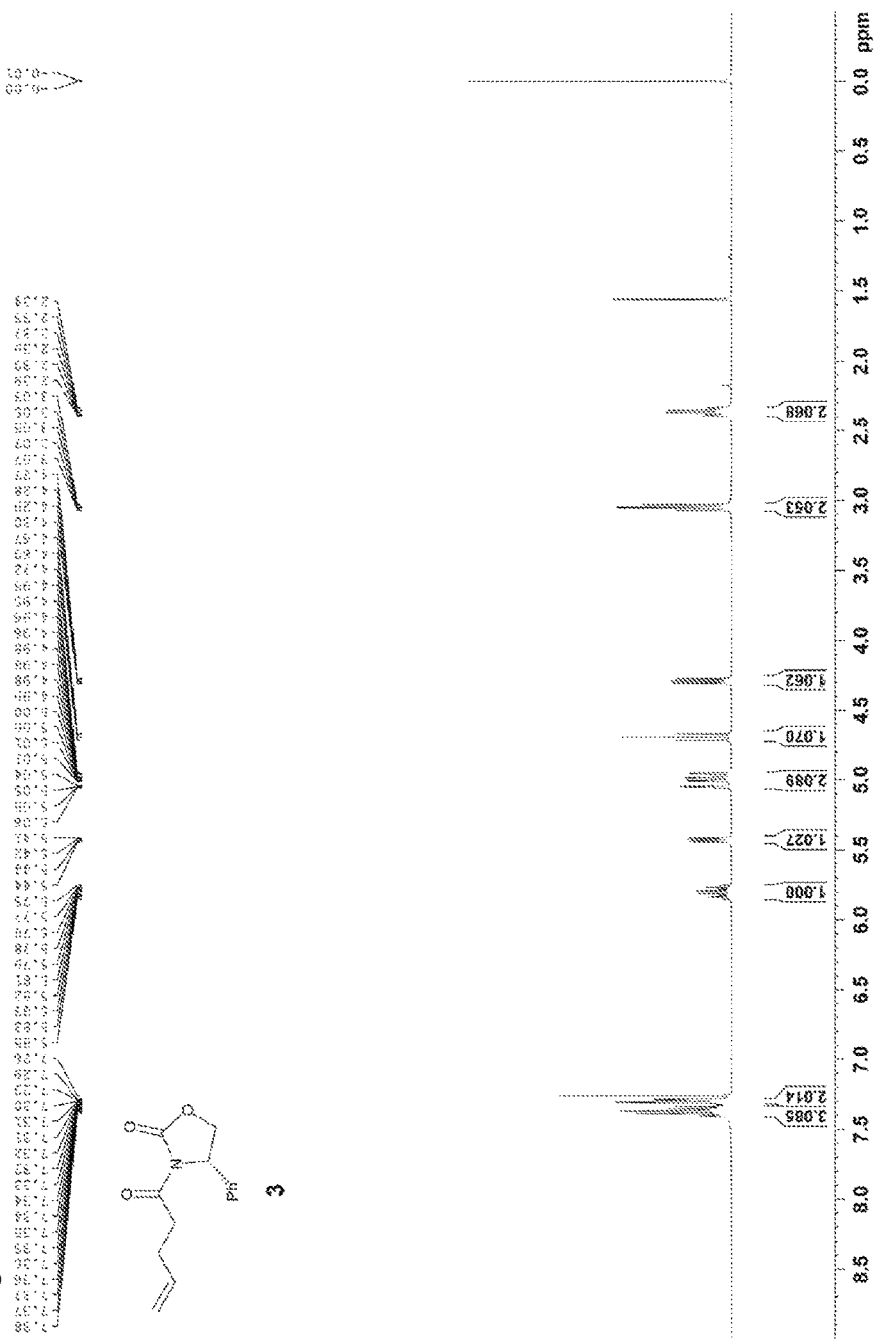

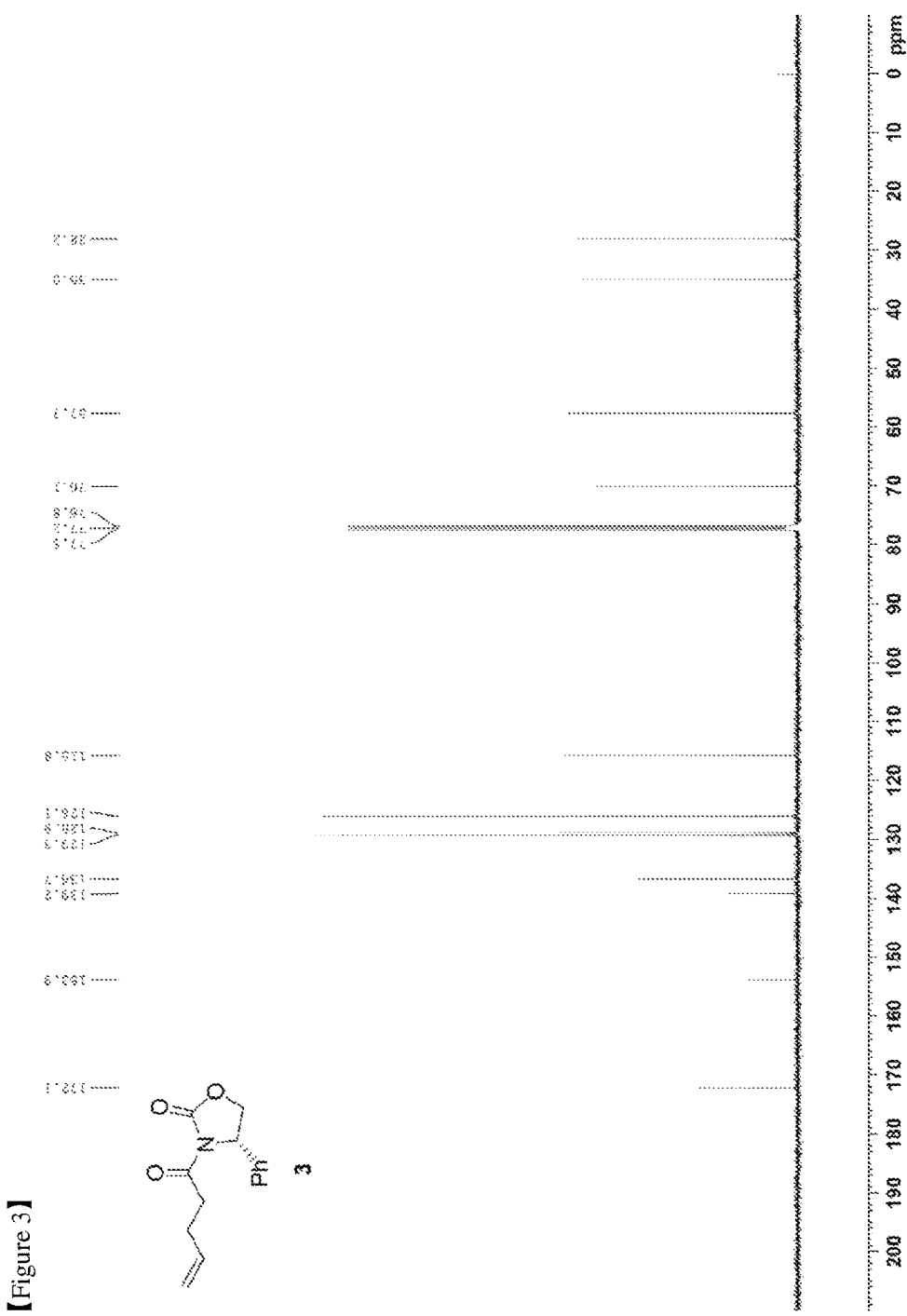
[Figure 3]

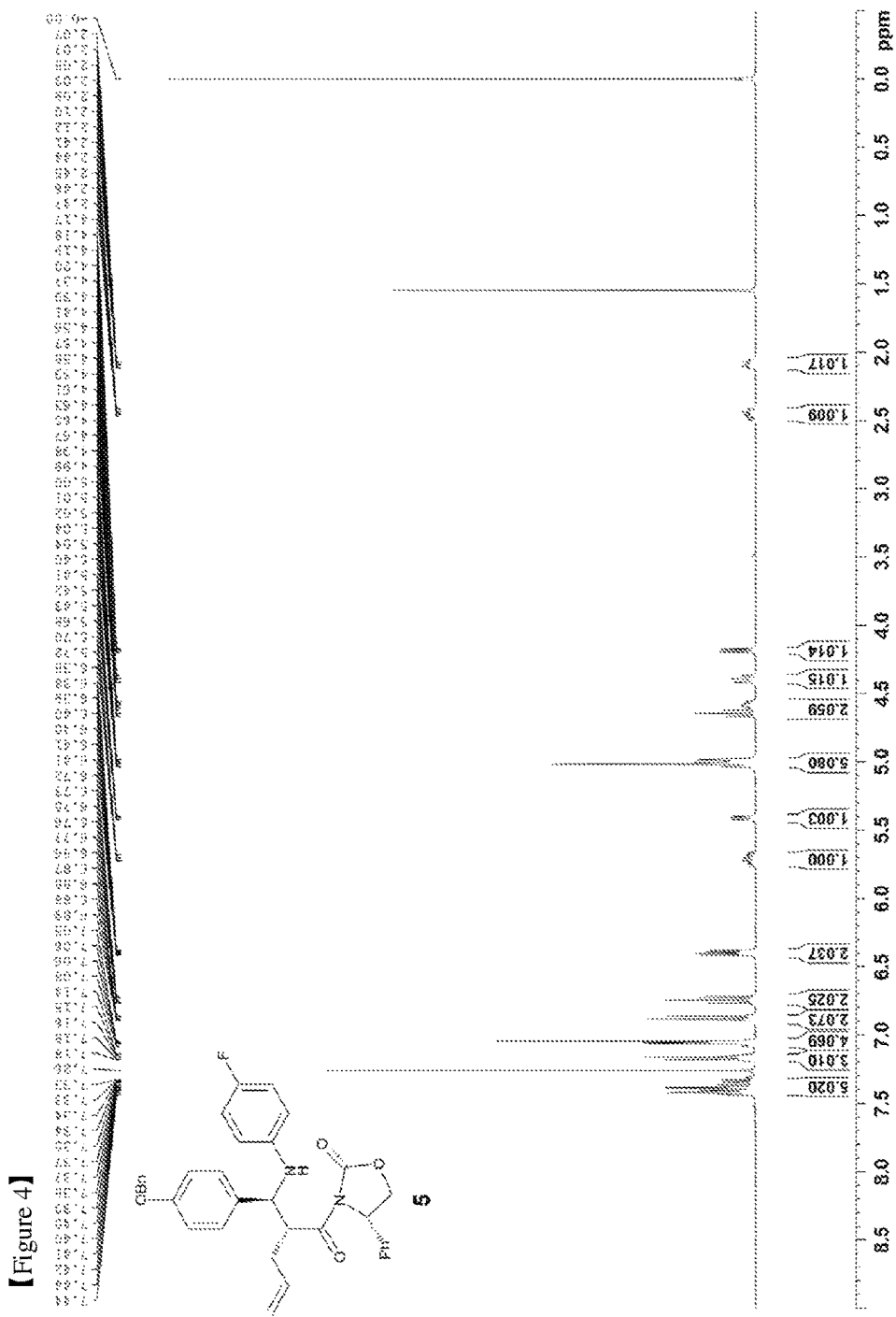

[Figure 5]
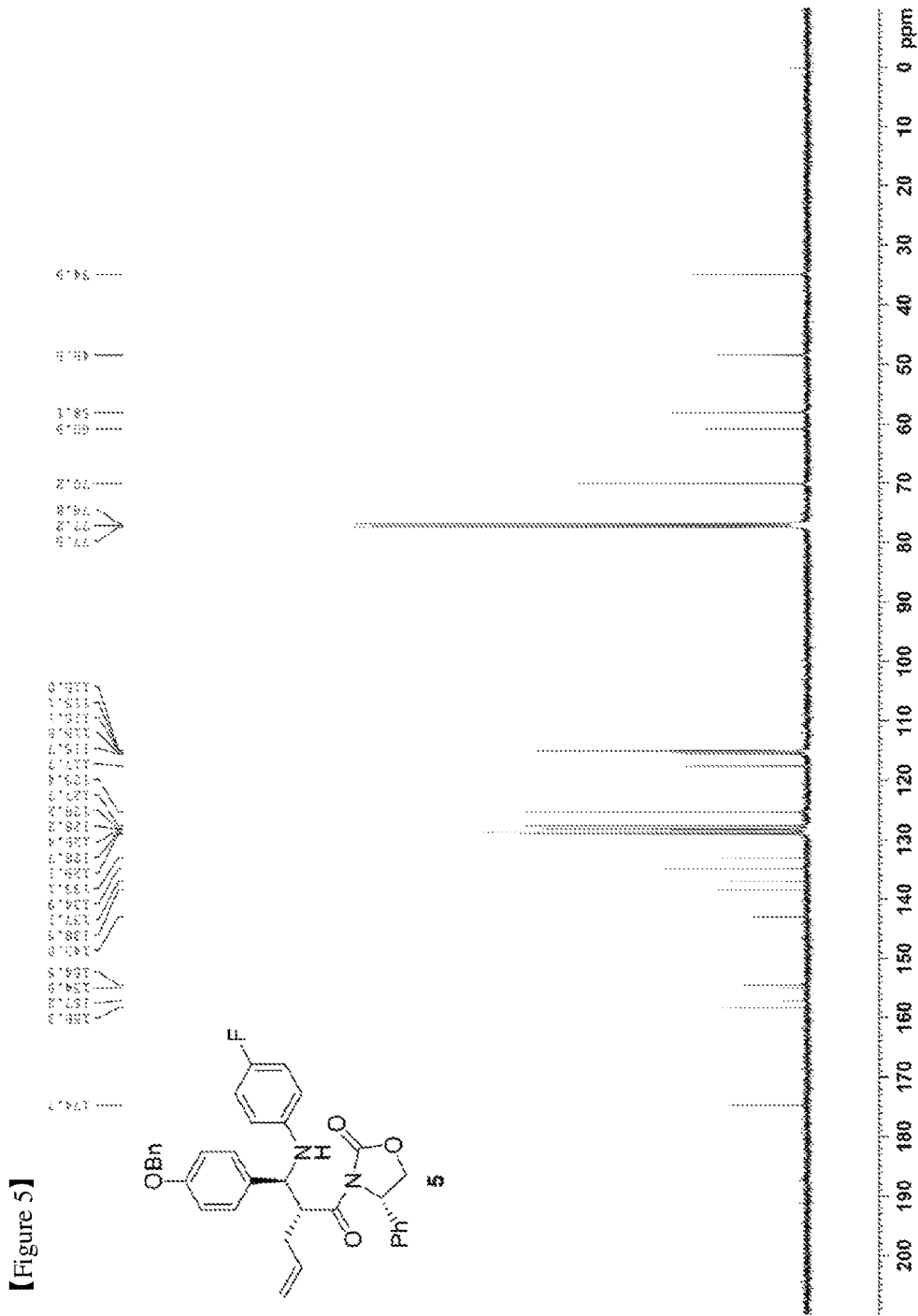

[Figure 6]
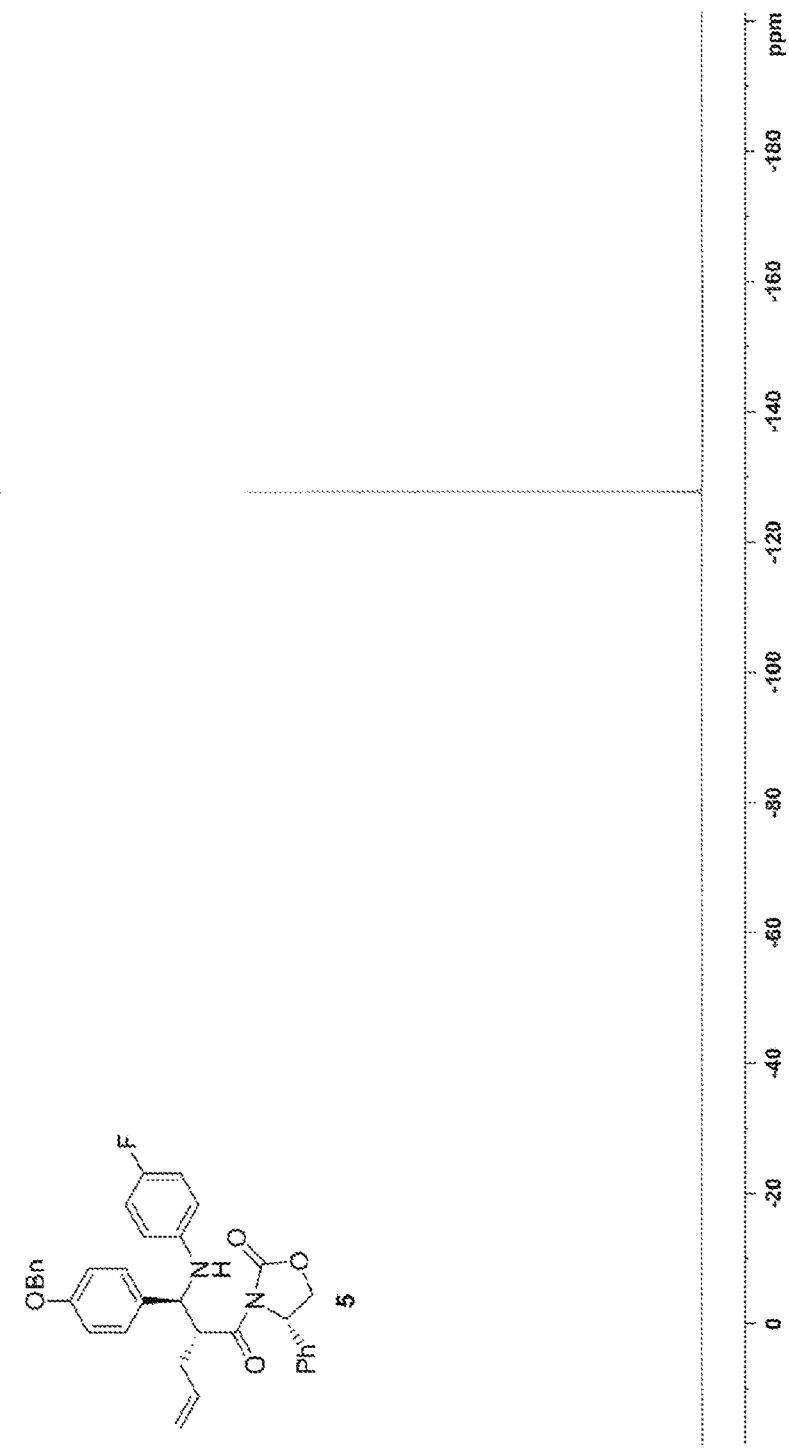

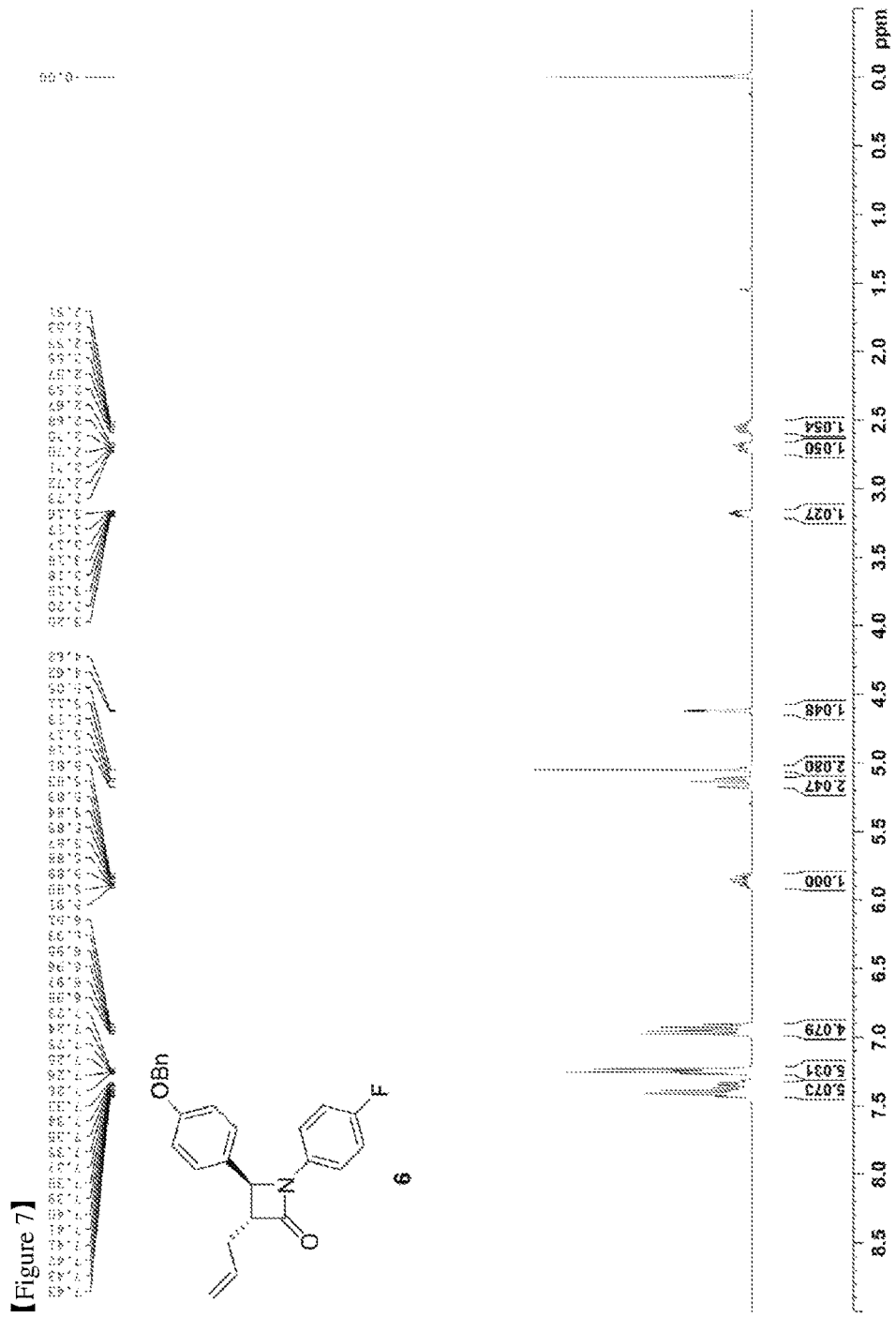
[Figure 7]

[Figure 8]
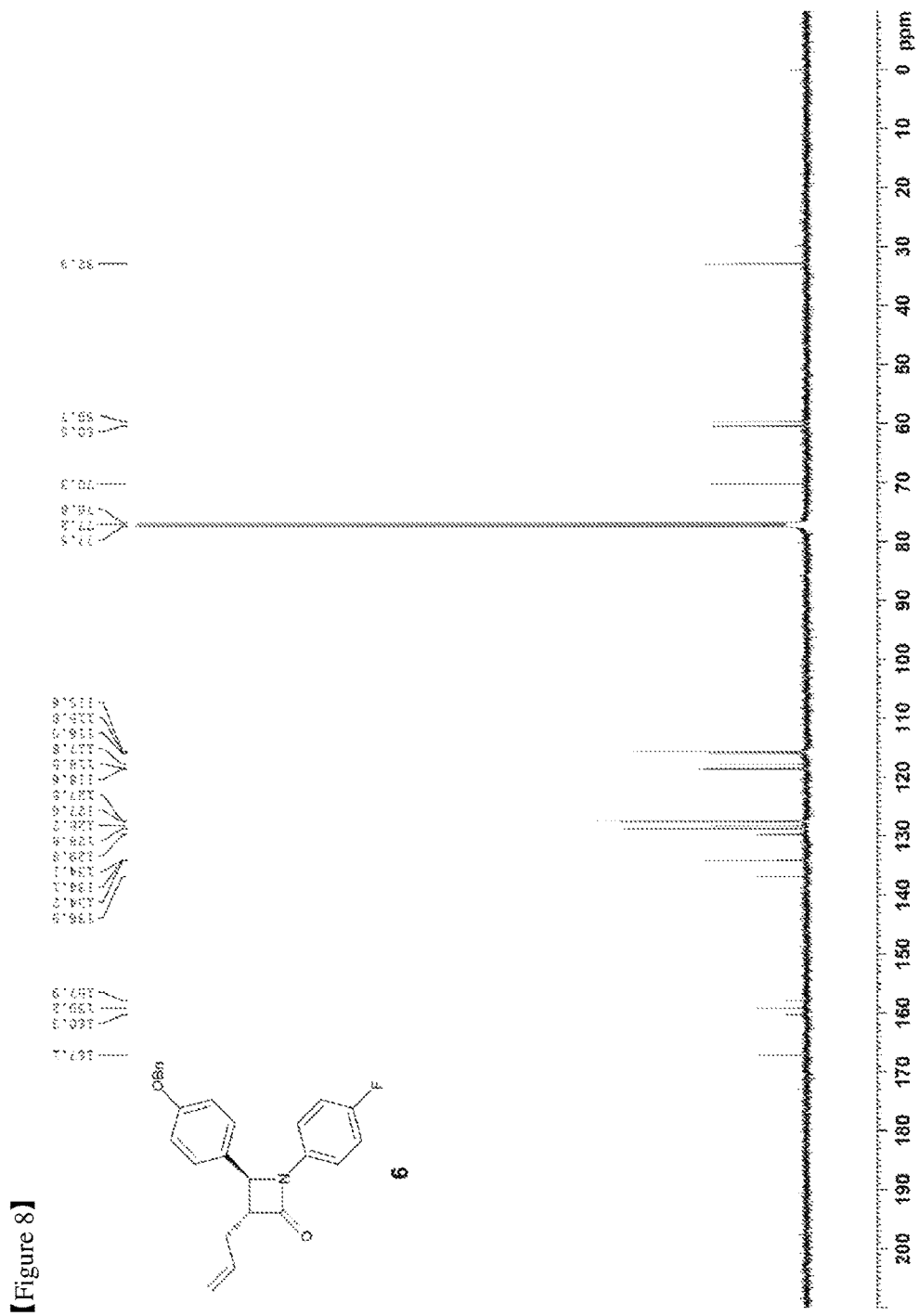

[Figure 9]
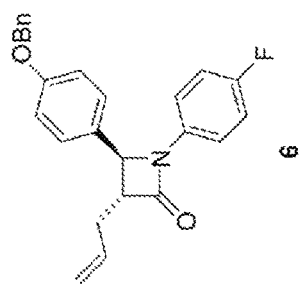
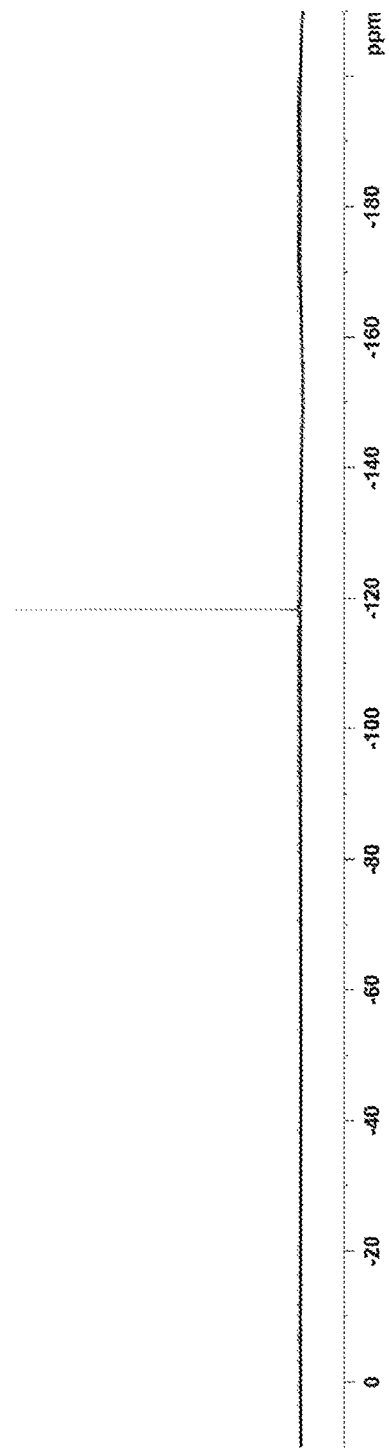

[Figure 10]
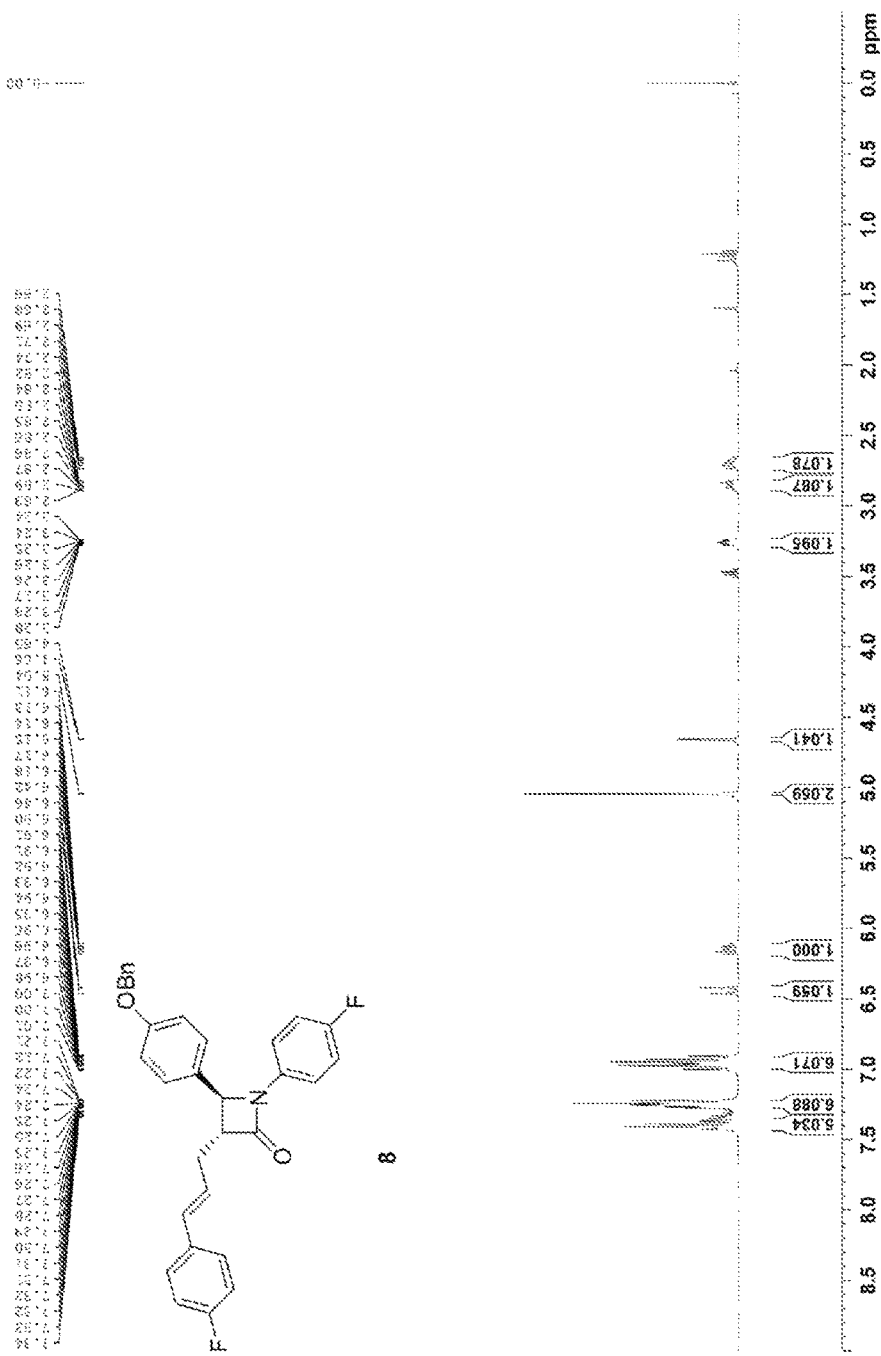

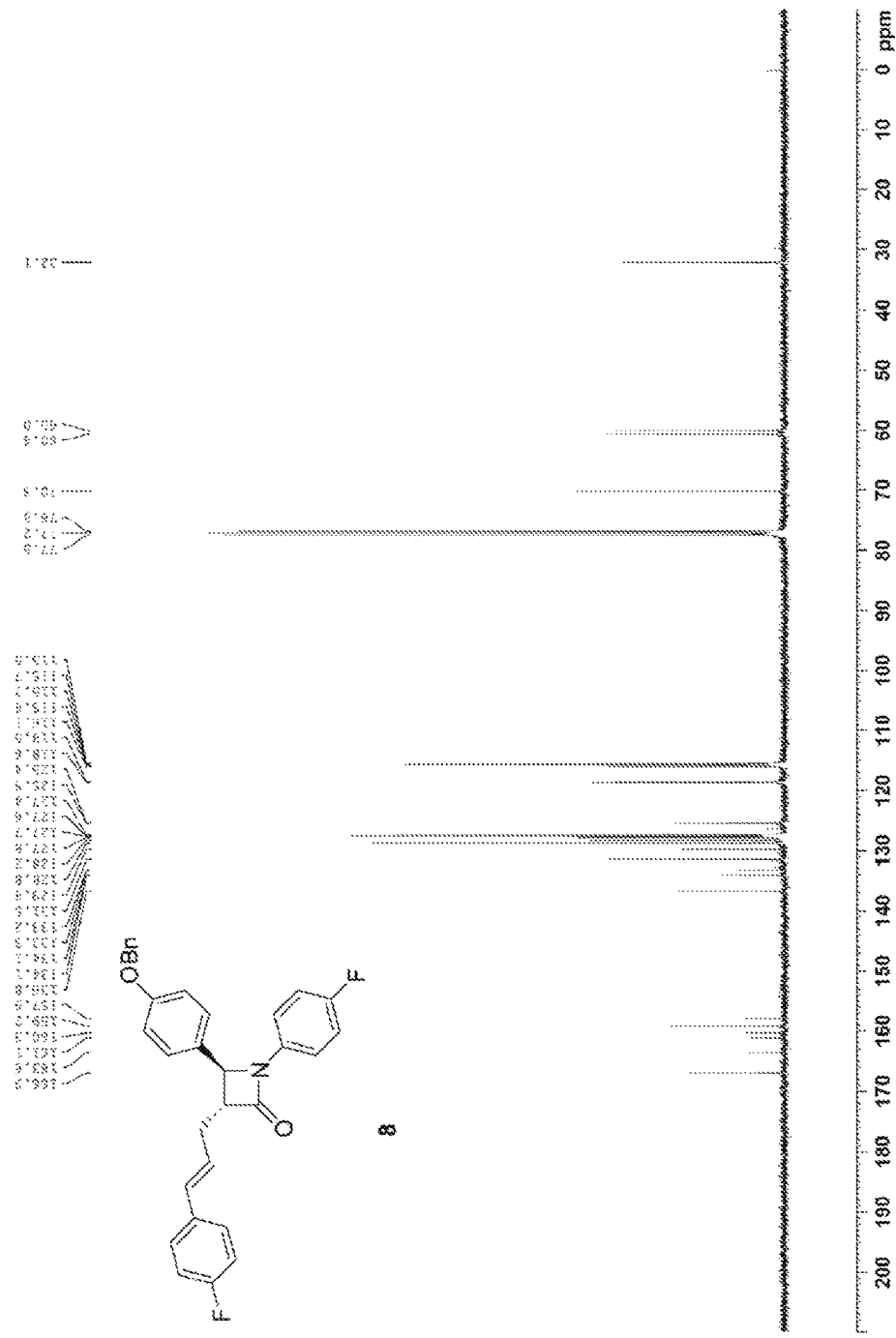
[Figure 11]

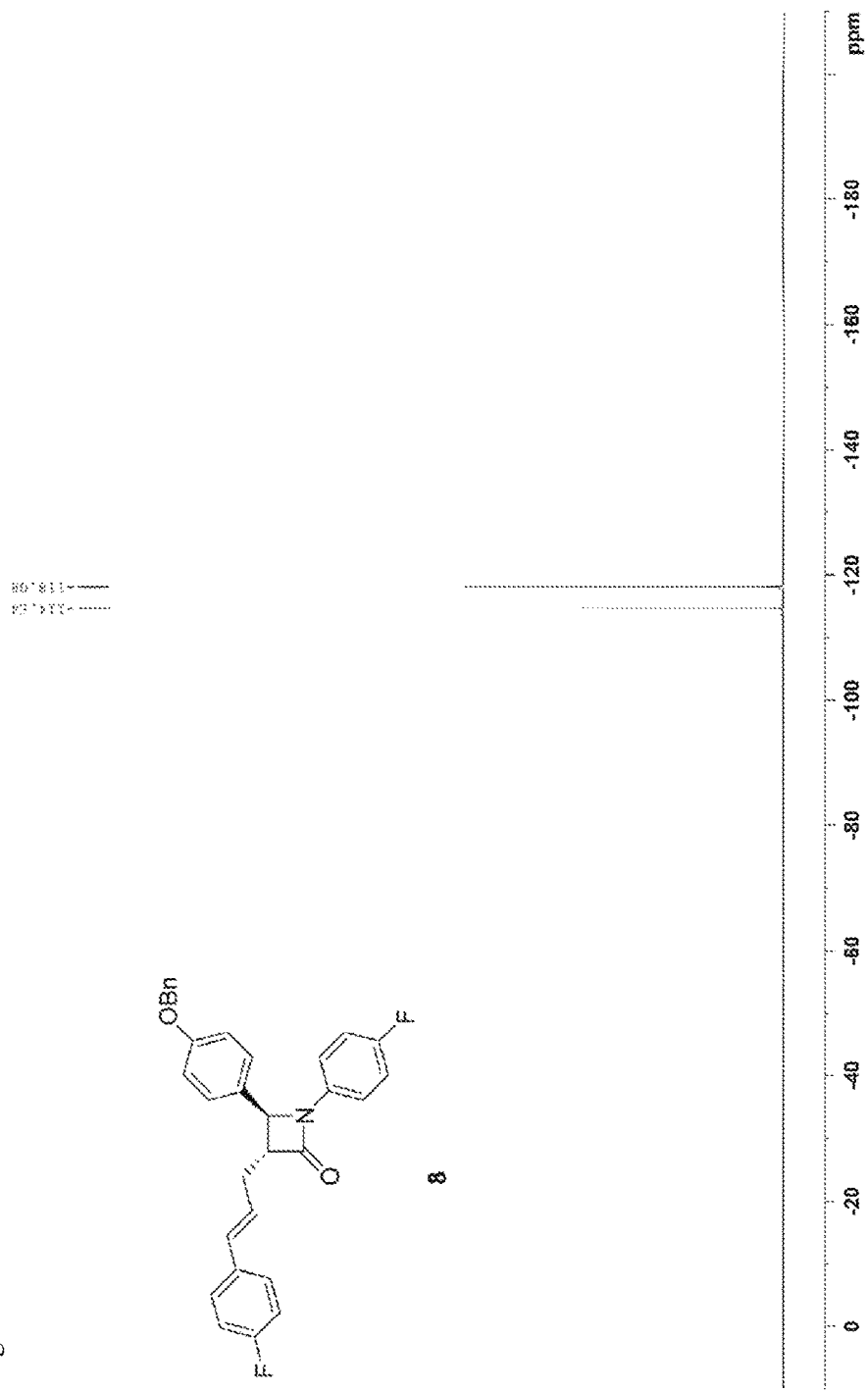
[Figure 12]

[Figure 13]
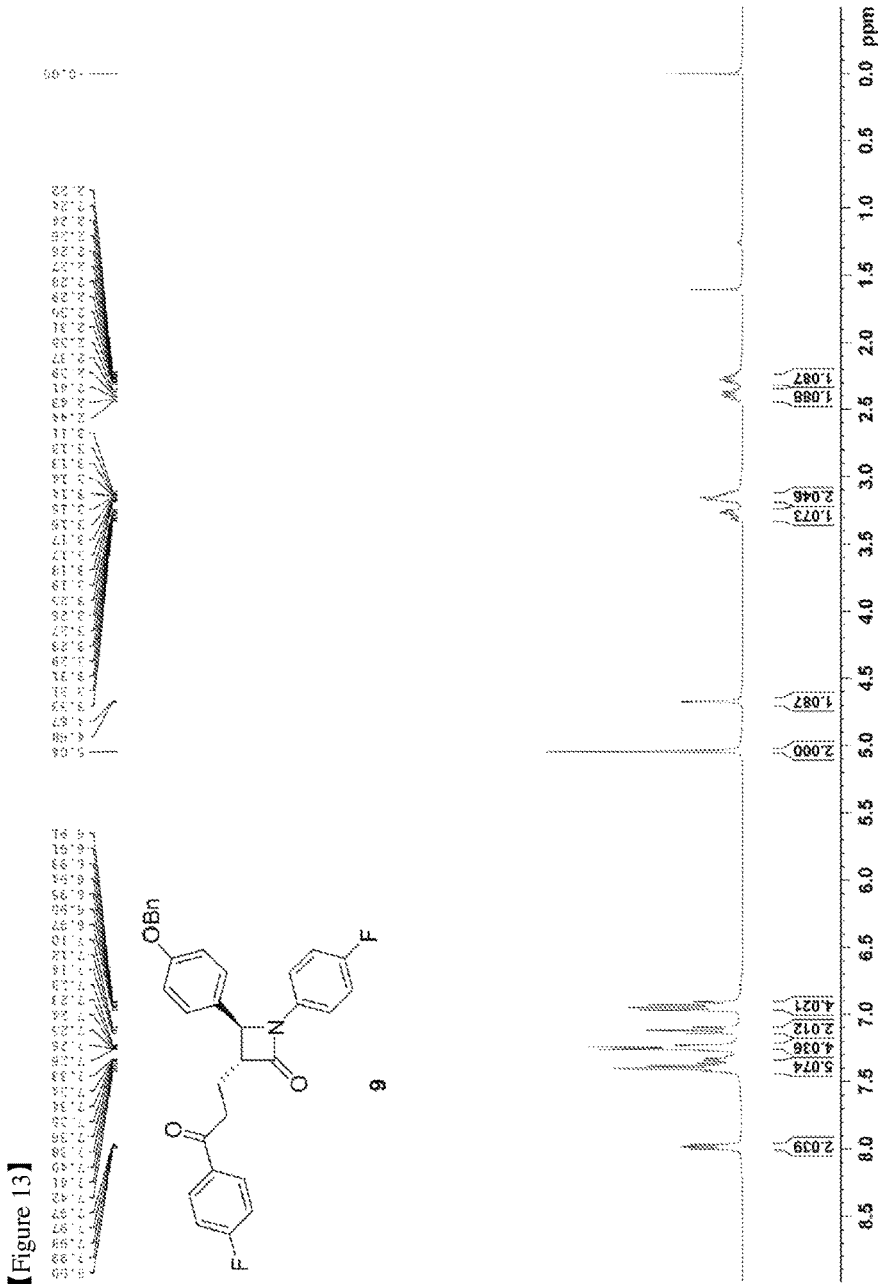

[Figure 14]
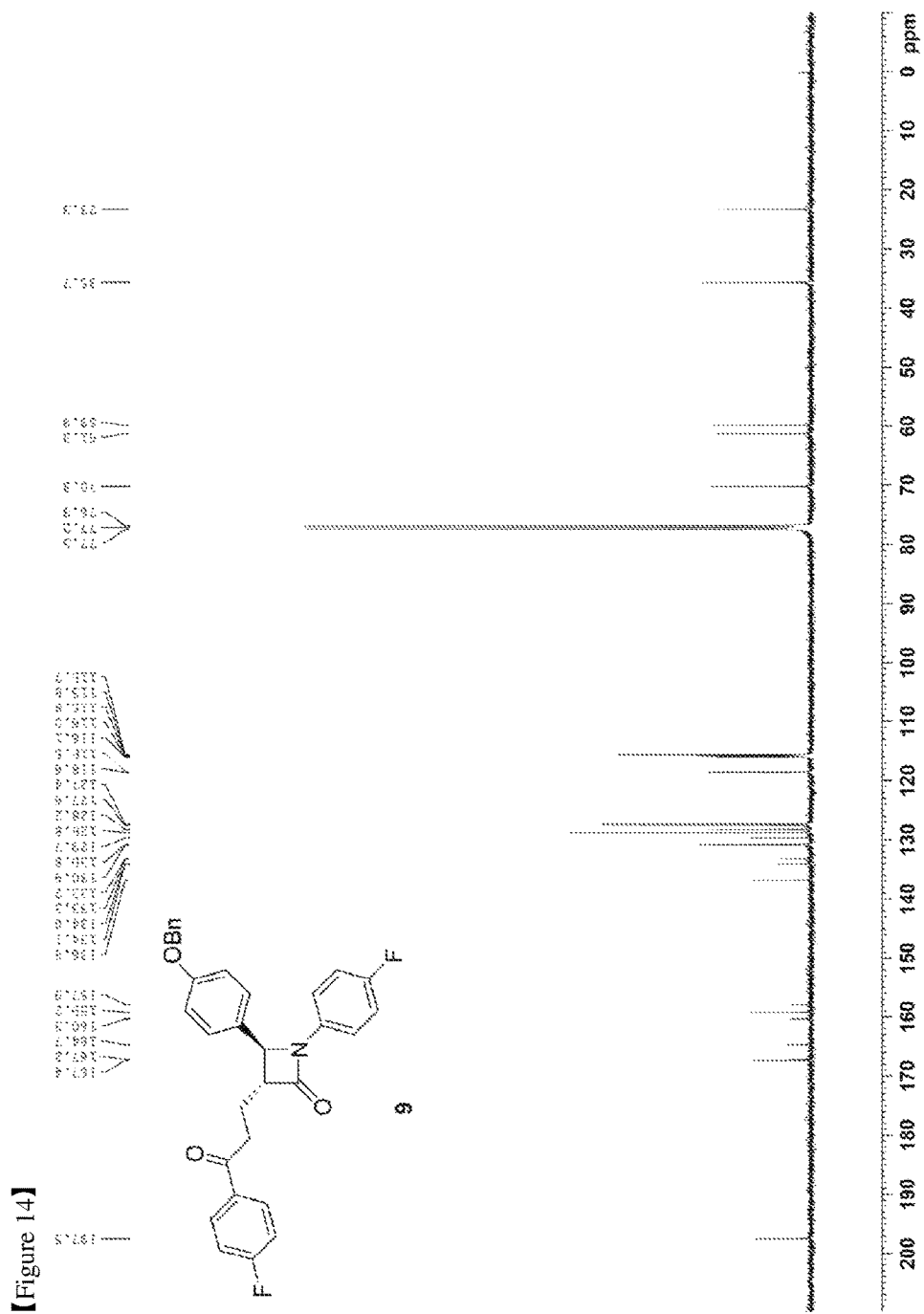

[Figure 15]
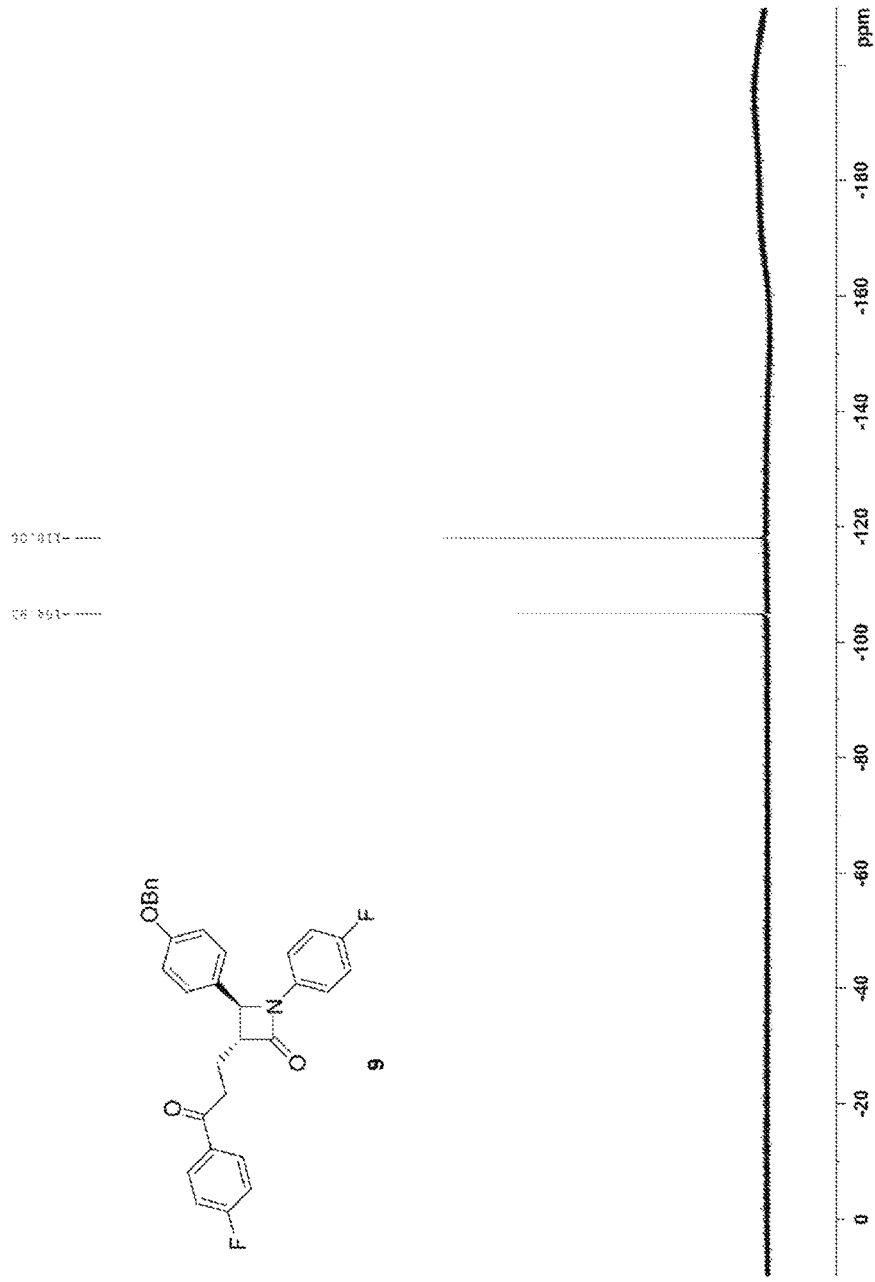

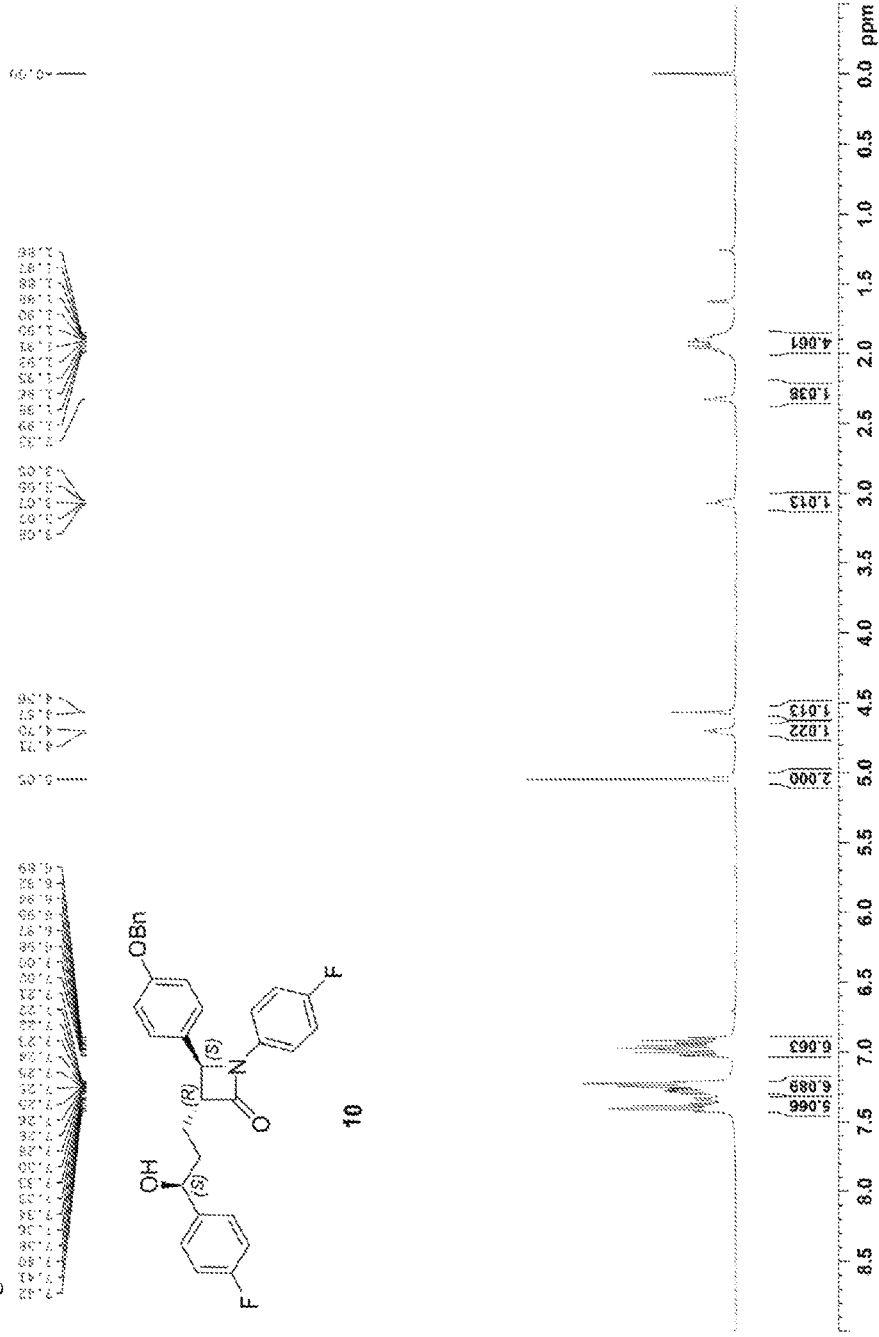

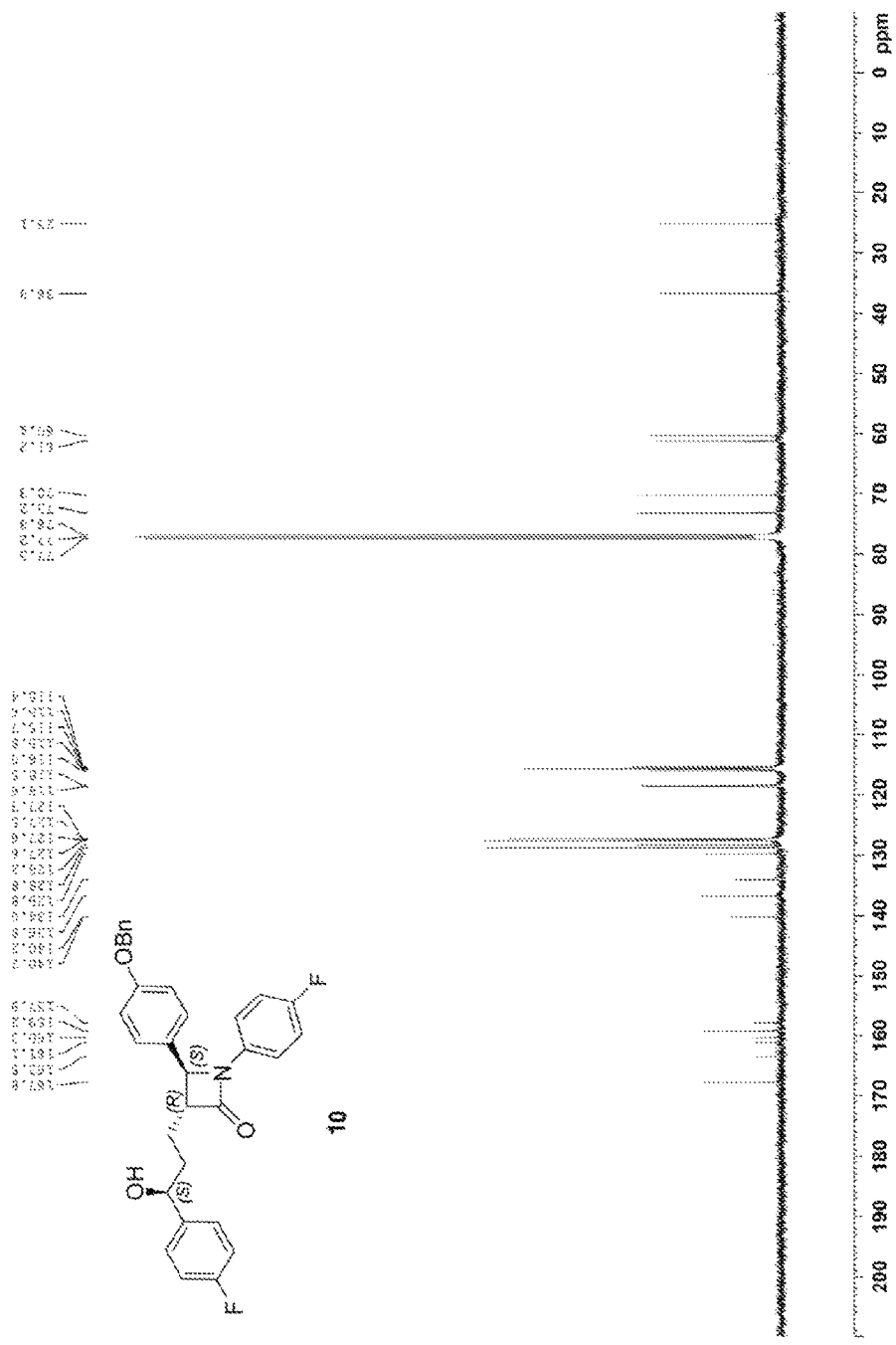
[Figure 17]

[Figure 18]
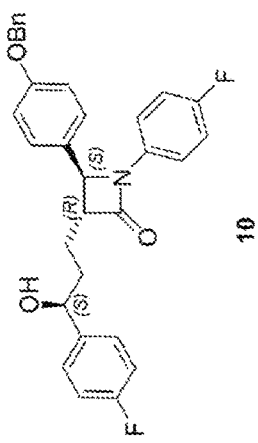
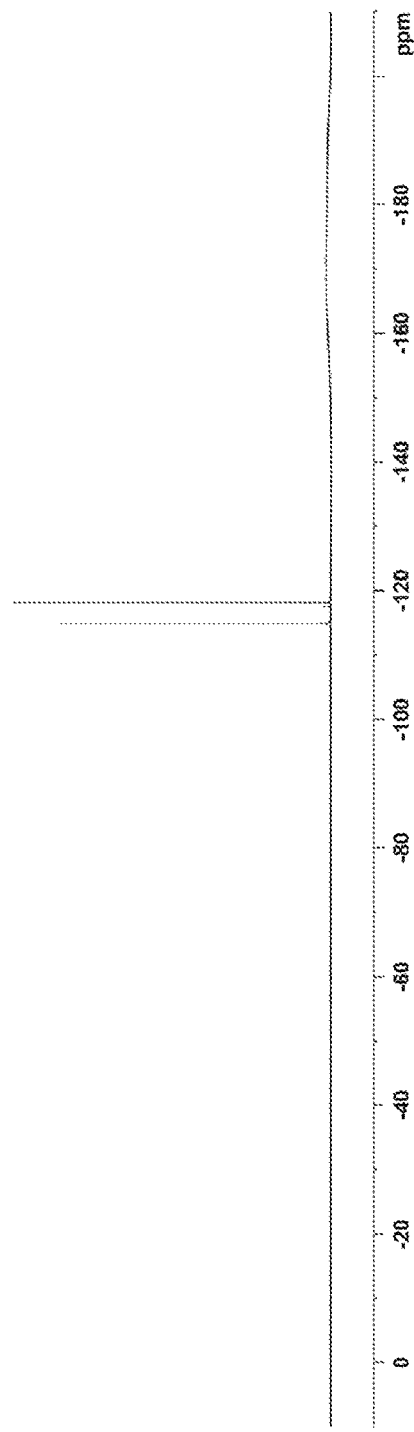

[Figure 19]
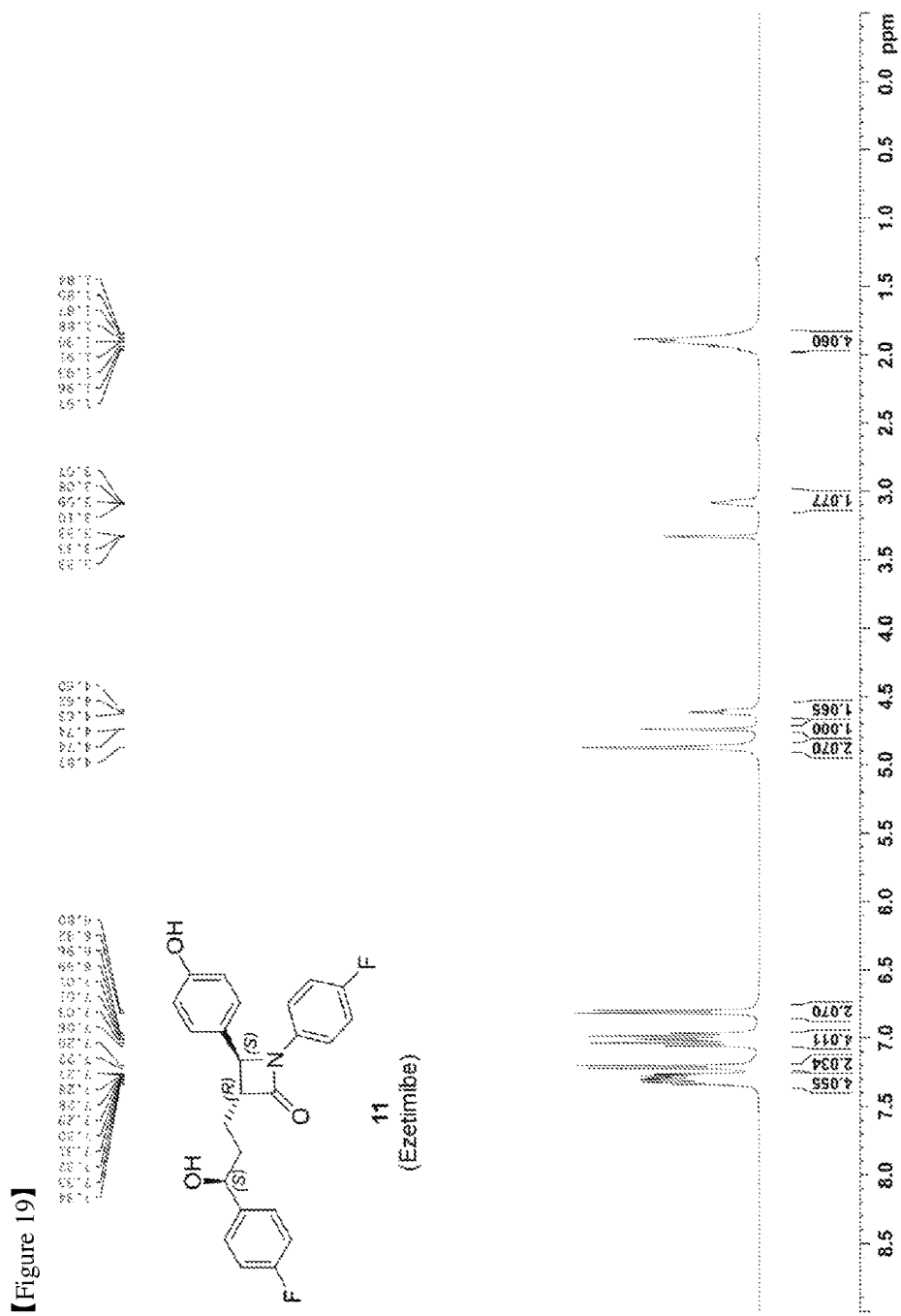

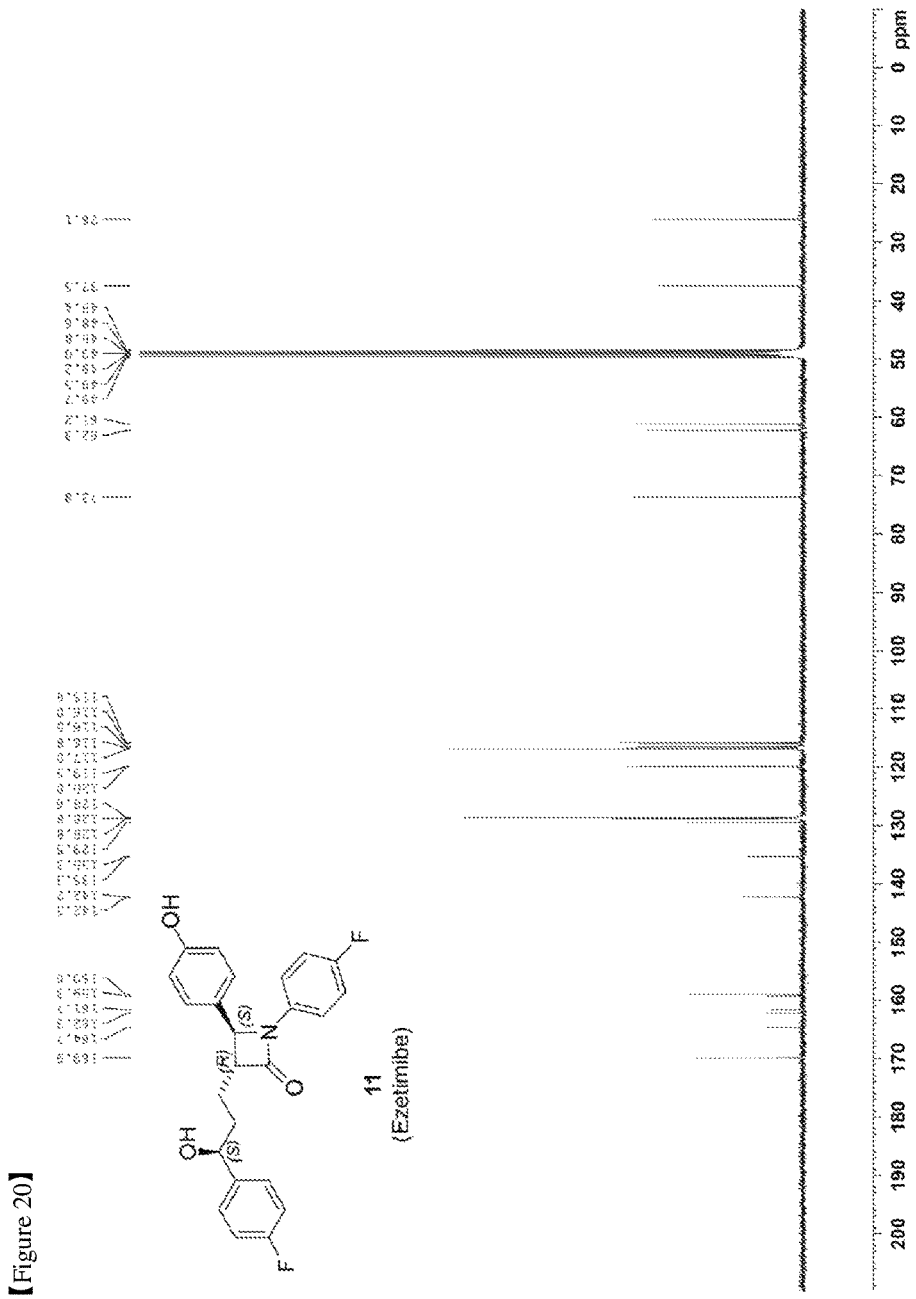
[Figure 20]

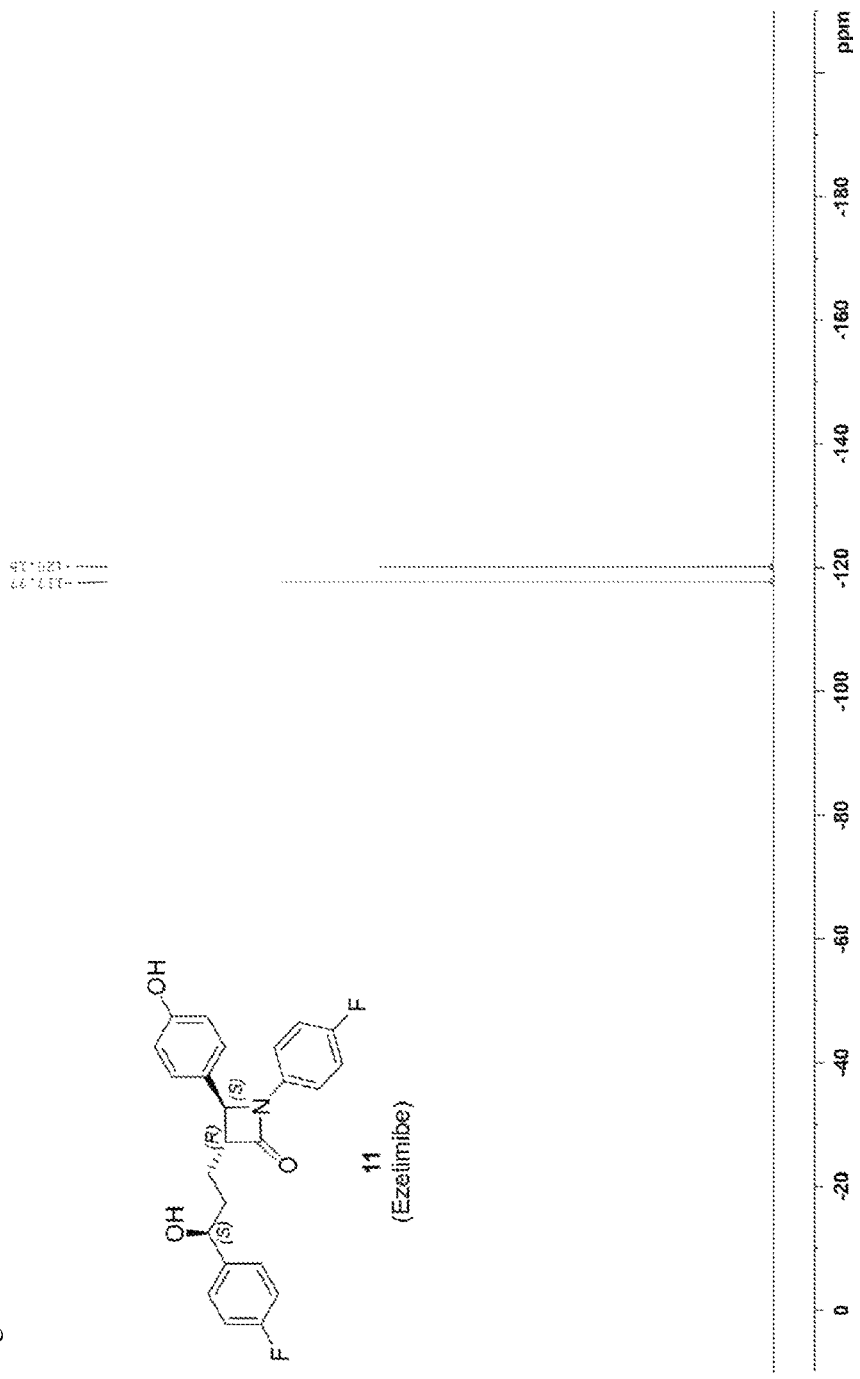
[Figure 21]

METHOD OF PREPARING EZETIMIBE AND INTERMEDIATE THEREOF

CROSS-REFERENCE TO RELATED APPLICATIONS

The present application claims priority under 35 U.S.C. § 119 to Korean Patent Application No. 10-2018-0020490, filed on Feb. 21, 2018, in the Korean Intellectual Property Office, the entire contents of each of which are hereby incorporated by reference.

TECHNICAL FIELD

The present invention relates to a novel method of preparing ezetimibe and an intermediate thereof, and more particularly to a method of preparing ezetimibe using a Grubbs $2^{nd}$ catalyst and a Pearlman's catalyst and to an intermediate thereof.

BACKGROUND ART

Ezetimibe (Chemical Formula a), which is a drug used as an inhibitor of cholesterol absorption in small intestine, is used as a main material of Ezetrol and Vytorin, which are commercially available drugs for the treatment of hyperlipidemia. The ezetimibe synthesis process, developed by Schering-Plough, is problematic because Grignard reagents and organolithium reagents, which are difficult to handle and have a risk of explosion, are used, and moreover, hydrogen gas at 2 atm and 4 atm is used upon reduction and deprotection reactions. Therefore, it is necessary to develop a new reaction capable of progressing under mild conditions to replace the reaction requiring such harsh conditions.
[Chemical Formula a]

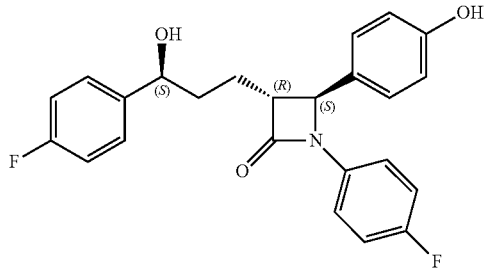

DISCLOSURE

Technical Problem

The present inventors have studied mild reaction conditions by alleviating harsh reaction conditions typically using Grignard and organolithium reagents in the synthesis of ezetimibe and thus have ascertained that ezetimibe may be synthesized by performing an intermolecular reaction under mild conditions through cross-metathesis using a Grubbs $2^{nd}$ catalyst and by conducting deprotection of a benzyl group under mild reaction conditions using hydrogen gas at atmospheric pressure in the presence of a Pearlman's catalyst.

Accordingly, the present invention is intended to provide a method of preparing ezetimibe including a cross-metathesis reaction using a Grubbs $2^{nd}$ catalyst and a deprotection reaction using a Pearlman's catalyst.

Technical Solution

Therefore, the present invention provides a method of preparing ezetimibe, which is a compound of Chemical Formula 11, comprising the following steps (1) to (7).

The method of preparing ezetimibe according to the present invention includes: (1) obtaining a compound of Chemical Formula 3 below by reacting a compound of Chemical Formula 1 below with a compound of Chemical Formula 2 below in the presence of DIPEA (diisopropylethylamine) and DMAP (dimethylaminopyridine); (2) obtaining a compound of Chemical Formula 5 below by reacting the compound of Chemical Formula 3 with a compound of Chemical Formula 4 below in the presence of $TiCl_4$ and DIPEA; (3) obtaining a compound of Chemical Formula 6 below by reacting the compound of Chemical Formula 5 in the presence of BSA (bis(trimethylsilyl)acetamide) and TBAF (tetrabutylammonium fluoride); (4) obtaining a compound of Chemical Formula 8 below by reacting the compound of Chemical Formula 6 with a compound of Chemical Formula 7 below in the presence of a Grubbs $2^{nd}$ catalyst and CuI; (5) obtaining a compound of Chemical Formula 9 below by reacting the compound of Chemical Formula 8 in the presence of $Pd(OAc)_2$, benzoquinone and $HClO_4$; (6) obtaining a compound of Chemical Formula 10 below by reacting the compound of Chemical Formula 9 in the presence of an (R)-CBS (Corey-Bakshi-Shibata) catalyst and a borane dimethyl sulfide complex; and (7) obtaining a compound of Chemical Formula 11 below by reacting the compound of Chemical Formula 10 in the presence of palladium hydroxide on carbon and cyclohexane.

[Chemical Formula 1]

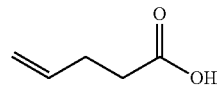

[Chemical Formula 2]

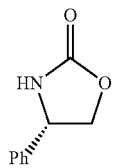

[Chemical Formula 3]

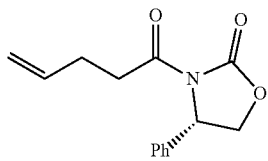

[Chemical Formula 4]

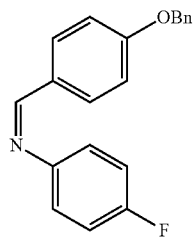

wherein Bn is benzyl.

[Chemical Formula 5]

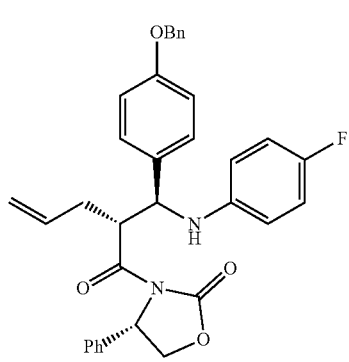

wherein Bn is benzyl.

[Chemical Formula 6]

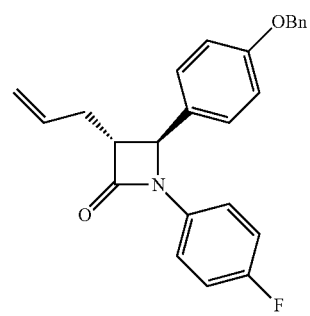

wherein Bn is benzyl.

[Chemical Formula 7]

[Chemical Formula 8]

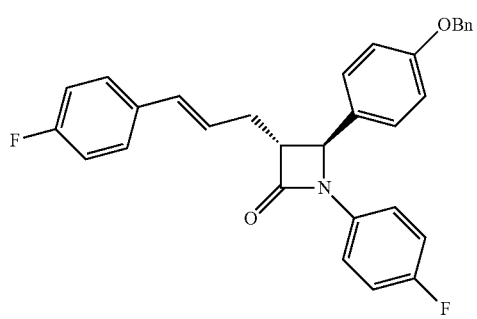

wherein Bn is benzyl.

[Chemical Formula 9]

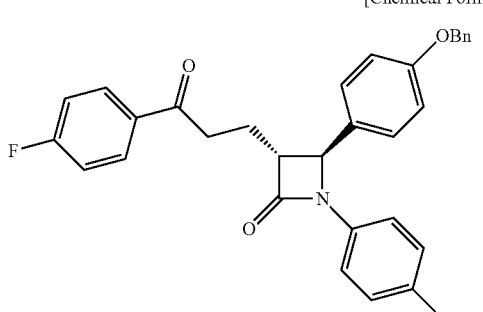

wherein Bn is benzyl.

[Chemical Formula 10]

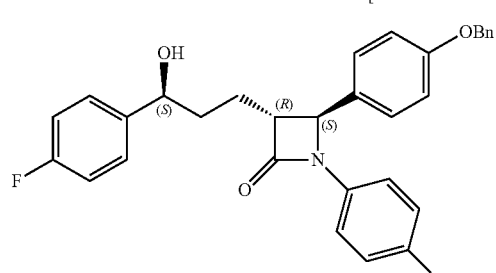

wherein Bn is benzyl.

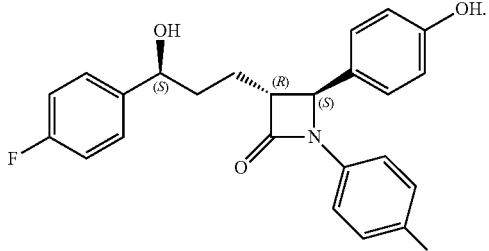

In addition, the present invention provides intermediates of the above preparation method, particularly a compound of Chemical Formula 4 below, a compound of Chemical Formula 5 below, a compound of Chemical Formula 6 below, a compound of Chemical Formula 8 below, a compound of Chemical Formula 9 below, and a compound of Chemical Formula 10 below.

[Chemical Formula 4]

wherein Bn is benzyl.

[Chemical Formula 5]

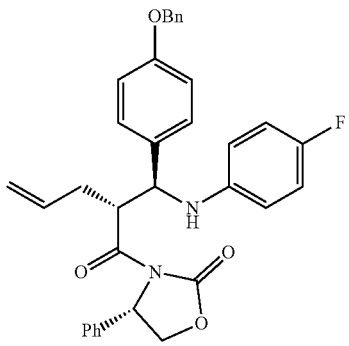

wherein Bn is benzyl.

[Chemical Formula 6]

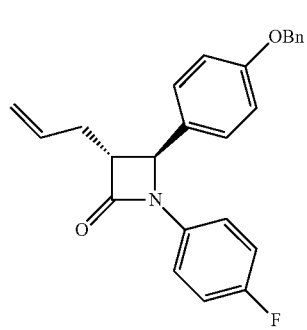

wherein Bn is benzyl.

[Chemical Formula 8]

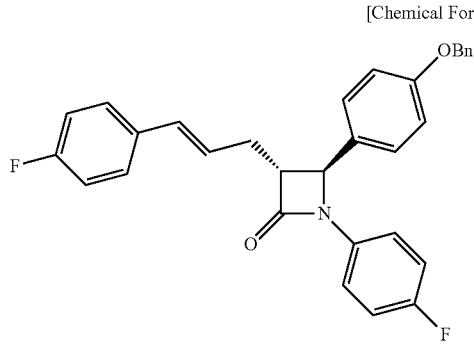

wherein Bn is benzyl.

[Chemical Formula 9]

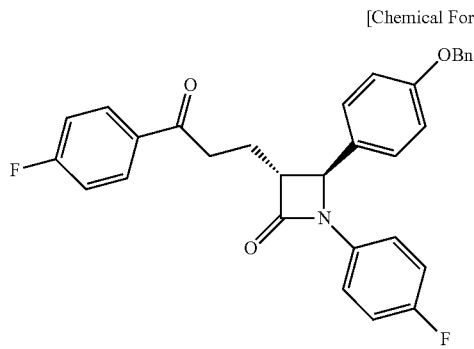

wherein Bn is benzyl.

[Chemical Formula 10]

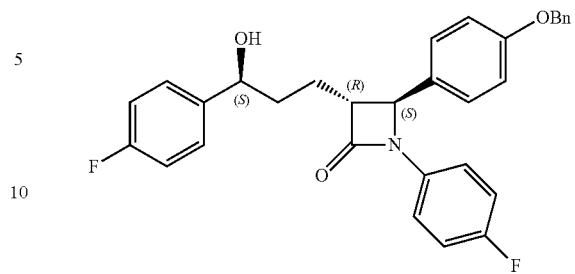

wherein Bn is benzyl.

Advantageous Effects

According to the present invention, a method of preparing ezetimibe includes a cross-metathesis reaction using a Grubbs $2^{nd}$ catalyst and a deprotection reaction using a Pearlman's catalyst, whereby intermolecular cross-metathesis is carried out under mild conditions, and mild conditions using hydrogen gas at atmospheric pressure are applied, thus synthesizing ezetimibe.

Also, the method of preparing ezetimibe according to the present invention is useful as an efficient ezetimibe synthesis technique in pharmaceutical fields using ezetimibe as a raw material.

DESCRIPTION OF DRAWINGS

FIG. 1 schematically shows the overall process of preparing ezetimibe according to the present invention;
FIG. 2 shows the $^1$H NMR spectrum of Compound 3;
FIG. 3 shows the $^{13}$C{$^1$H} NMR spectrum of Compound 3;
FIG. 4 shows the $^1$H NMR spectrum of Compound 5;
FIG. 5 shows the $^{13}$C{$^1$H} NMR spectrum of Compound 5;
FIG. 6 shows the $^{19}$F NMR spectrum of Compound 5;
FIG. 7 shows the $^1$H NMR spectrum of Compound 6;
FIG. 8 shows the $^{13}$C{$^1$H} NMR spectrum of Compound 6;
FIG. 9 shows the $^{19}$F NMR spectrum of Compound 6;
FIG. 10 shows the $^1$H NMR spectrum of Compound 8;
FIG. 11 shows the $^{13}$C{$^1$H} NMR spectrum of Compound 8;
FIG. 12 shows the $^{19}$F NMR spectrum of Compound 8;
FIG. 13 shows the $^1$H NMR spectrum of Compound 9;
FIG. 14 shows the $^{13}$C{$^1$H} NMR spectrum of Compound 9;
FIG. 15 shows the $1^9$F NMR spectrum of Compound 9;
FIG. 16 shows the $^1$H NMR spectrum of Compound 10;
FIG. 17 shows the $^{13}$C{$^1$H} NMR spectrum of Compound 10;
FIG. 18 shows the $^{19}$F NMR spectrum of Compound 10;
FIG. 19 shows the $^1$H NMR spectrum of Compound 11;
FIG. 20 shows the $^{13}$C{$^1$H} NMR spectrum of Compound 11; and
FIG. 21 shows the $^{19}$F NMR spectrum of Compound 11.

BEST MODE

According to the present invention, a method of preparing ezetimibe may be performed as shown in FIG. 1. Specifically, the method of preparing ezetimibe according to the present invention includes performing an intermolecular reaction under mild conditions through cross-metathesis using a Grubbs $2^{nd}$ catalyst [step (4)], and performing deprotection of a benzyl group in the presence of a Pearlman's catalyst under mild conditions using hydrogen gas at atmospheric pressure [step (7)], whereby ezetimibe is synthesized.

<Step (1)>

Step (1) is obtaining a compound of Chemical Formula 3 by reacting a compound of Chemical Formula 1 with a compound of Chemical Formula 2 in the presence of DIPEA (diisopropylethylamine) and DMAP (dimethylaminopyridine).

Specifically, pent-4-enoic acid (Compound 1) and oxalyl chloride are added to a solvent (e.g. DCM), added with DMF, reacted at about 40° C. (i.e. within the range from 30 to 50° C.), and then cooled to room temperature, after which the solvent is removed. Thereafter, the resulting product is added with a solvent and is reacted with a solution of (S)-4-phenyloxazolidin-2-one (Compound 2) and DMAP dissolved in the above solvent, thus obtaining (S)-3-(pent-4-enoyl)-4-phenyloxazolidin-2-one (Compound 3).

In the above reaction, oxalyl chloride may be used in an amount of 0.5 to 2 equivalents, preferably 1 to 1.5 equivalents, and more preferably 1.2 equivalents, based on the amount of Compound 1.

Also, DIPEA may be used in an amount of 1 to 3 equivalents, preferably 1.5 to 2.5 equivalents, and more preferably 2 equivalents, based on the amount of Compound 1.

Also, DMAP may be used in an amount of 1 to 10 mol %, preferably 3 to 7 mol %, and more preferably 5 mol %, based on the amount of Compound 1.

<Step (2)>

Step (2) is obtaining a compound of Chemical Formula 5 by reacting the compound of Chemical Formula 3 with a compound of Chemical Formula 4 in the presence of $TiCl_4$ and DIPEA.

Specifically, Compound 3 is dissolved in a solvent (e.g. DCM), cooled to about −20° C. (i.e. within the range from −30 to −10° C.), added with $TiCl_4$, reacted, added with DIPEA, and reacted. The resulting reaction product is added to a solution of (Z)-1-(4-(benzyloxy)phenyl)-N-(4-fluorophenyl)methaneimine (Compound 4) in DCM, and is then reacted at about −20° C. (i.e. within the range from −30 to −10° C.), thus obtaining (S)-3-((R)-2-((S)-(4-(benzyloxy)phenyl) ((4-fluorophenyl)amino)methyl)pent-4-enoyl)-4-phenyloxazolidin-2-one (Compound 5).

In the above reaction, $TiCl_4$ may be used in an amount of 0.5 to 2 equivalents, preferably 1 to 1.5 equivalents, and more preferably 1.1 equivalents, based on the amount of Compound 3.

Also, DIPEA may be used in an amount of 1 to 3 equivalents, preferably 1.5 to 2.5 equivalents, and more preferably 2 equivalents, based on the amount of Compound 3.

<Step (3)>

Step (3) is obtaining a compound of Chemical Formula 6 by reacting the compound of Chemical Formula 5 in the presence of BSA (bis(trimethylsilyl)acetamide) and TBAF (tetrabutylammonium fluoride).

Specifically, Compound 5 is added to a solvent (e.g. toluene), added with BSA, reacted at room temperature, added with TBAF·$3H_2O$, and reacted, thus obtaining (3R,4S)-3-allyl-4-(4-(benzyloxy)phenyl)-1-(4-fluorophenyl)azetidin-2-one (Compound 6).

In the above reaction, BSA may be used in an amount of 1 to 3 equivalents, preferably 1.5 to 2.5 equivalents, and more preferably 2 equivalents, based on the amount of Compound 5.

Also, TBAF may be used in an amount of 1 to 10 mol %, preferably 3 to 7 mol %, and more preferably 5 mol %, based on the amount of Compound 5.

<Step (4)>

Step (4) is obtaining a compound of Chemical Formula 8 by reacting the compound of Chemical Formula 6 with a compound of Chemical Formula 7 in the presence of a Grubbs $2^{nd}$ catalyst and CuI.

Specifically, Compound 6, 1-fluoro-4-vinylbenzene (Compound 7), a Grubbs $2^{nd}$ catalyst and CuI are added to a solvent (e.g. ether), reacted at about 40° C. (i.e. within the range from 30 to 50° C.), cooled to room temperature, and filtered through silica gel, thus obtaining (3R,4S)-4-(4-(benzyloxy)phenyl)-1-(4-fluorophenyl)-3-((E)-3-(4-fluorophenyl)allyl)azetidin-2-one (Compound 8).

In the above reaction, the Grubbs $2^{nd}$ catalyst may be used in an amount of 1 to 10 mol %, preferably 3 to 7 mol %, and more preferably 5 mol %, based on the amount of Compound 7.

Also, CuI may be used in an amount of 1 to 50 mol %, preferably 5 to 20 mol %, and more preferably 10 mol %, based on the amount of Compound 7.

<Step (5)>

Step (5) is obtaining a compound of Chemical Formula 9 by reacting the compound of Chemical Formula 8 in the presence of $Pd(OAc)_2$, benzoquinone and $HClO_4$.

Specifically, $Pd(OAc)_2$, benzoquinone and $HClO_4$ are added to a solvent (e.g. acetonitrile), deoxygenated with stirring, added with Compound 8 dissolved in a solvent, and reacted, thus obtaining (3R,4S)-4-(4-(benzyloxy)phenyl)-1-(4-fluorophenyl)-3-(3-(4-fluorophenyl)-3-oxopropyl)azetidin-2-one (Compound 9).

In the above reaction, benzoquinone may be used in an amount of 0.5 to 5 equivalents, preferably 1 to 2 equivalents, and more preferably 1.5 equivalents, based on the amount of Compound 8.

Also, $Pd(OAc)_2$ may be used in an amount of 1 to 10 mol %, preferably 1 to 5 mol %, and more preferably 3 mol %, based on the amount of Compound 8.

<Step (6)>

Step (6) is obtaining a compound of Chemical Formula 10 by reacting the compound of Chemical Formula 9 in the presence of a (R)-CBS catalyst and a borane dimethyl sulfide complex.

Specifically, the (R)-CBS (Corey-Bakshi-Shibata) catalyst and Compound 9 are dissolved in a solvent (e.g. THF), stirred at about −20° C. (i.e. within the range from −30 to −10° C.), added with the borane dimethyl sulfide complex, and reacted at about −20° C. (i.e. within the range from −30 to −10° C.), thus obtaining (3R,4S)-4-(4-(benzyloxy)phenyl)-1-(4-fluorophenyl)-3-((S)-3-(4-fluorophenyl)-3-hydroxypropyl)azetidin-2-one (Compound 10).

In the above reaction, the (R)-CBS catalyst may be used in an amount of 1 to 50 mol %, preferably 10 to 30 mol %, and more preferably 20 mol %, based on the amount of Compound 9.

Also, the borane dimethyl sulfide complex may be used in an amount of 0.5 to 5 equivalents, preferably 1 to 2 equivalents, and more preferably 1.2 equivalents, based on the amount of Compound 9.

<Step (7)>

Step (7) is obtaining a compound of Chemical Formula 11 by reacting the compound of Chemical Formula 10 in the presence of palladium hydroxide on carbon (a Pearlman's catalyst) and cyclohexane.

Here, Compound 10, Pd(OH)$_2$/C (palladium hydroxide on carbon) and cyclohexane are added to a solvent (e.g. MeOH) under hydrogen gas (H$_2$) at about 1 atm (i.e. within the range from 0.5 to 1.5 atm), and reacted at about 70° C. (i.e. within the range from 60 to 80° C.), thus obtaining (3R,4S)-1-(4-fluorophenyl)-3-((S)-3-(4-fluorophenyl)-3-hydroxypropyl)-4-(4-hydroxyphenyl)azetidin-2-one (Compound 11).

In the above reaction, Pd(OH)$_2$/C may be used in an amount of 1 to 30 mol %, preferably 10 to 20 mol %, and more preferably 15 mol %, based on the amount of Compound 10.

Also, cyclohexane may be used in an amount of 0.5 to 5 equivalents, preferably 1 to 2 equivalents, and more preferably 1.1 equivalents, based on the amount of Compound 10.

A better understanding of the present invention will be given through the following example, which is merely set forth to illustrate the present invention but is not to be construed as limiting the scope of the present invention.

Example

Step (1): Synthesis of (S)-3-(pent-4-enoyl)-4-phenyloxazolidin-2-one (Compound 3)

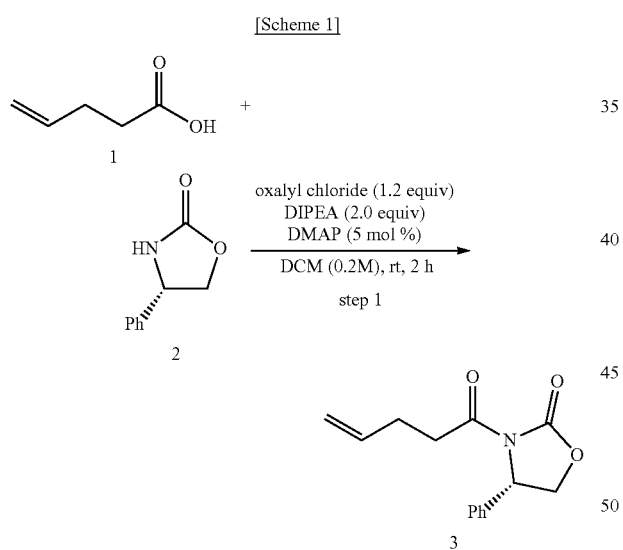

Pent-4-enoic acid (1, 2.04 mL, 20 mmol) was dissolved in a DCM (dichloromethane) solvent (66 mL) and oxalyl chloride (2.03 mL, 24 mmol) was then added dropwise thereto. Subsequently, DMF (dimethylformamide) (200 µL) was added thereto, and the reaction was carried out at 40° C. for 1 hr. The reaction solution was cooled to room temperature and the solvent was removed therefrom using an evaporator. Subsequently, the resulting product was diluted with DCM (66 mL) and was then added dropwise to a solution of (S)-4-phenyloxazolidin-2-one (2, 3590 mg, 22 mmol), DIPEA (diisopropylethylamine) (6968 µL, 40 mmol), and DMAP (dimethylaminopyridine) (122.17 mg, 1 mmol) dissolved in DCM (36.6 mL). The resulting reaction solution was stirred at room temperature for 2 hr. After completion of the reaction, the reaction was terminated with 0.5 M HCl (50 mL), followed by extraction with DCM (60 mL, 20 mL×3). The DCM layer was dried with anhydrous MgSO$_4$ and then filtered. Further, column chromatography (ethyl acetate:hexane=1:2) was performed, thus yielding a desired compound (S)-3-(pent-4-enoyl)-4-phenyloxazolidin-2-one (3, 4219 mg, 86%) (FIGS. 2 and 3).

(S)-3-(pent-4-enoyl)-4-phenyloxazolidin-2-one (3)

4219 mg, 86%, White solid; Rf=0.5 (ethyl acetate:hexane=1:2); $^1$H NMR (400 MHz, CDCl$_3$) δ 7.41-7.29 (m, 5H), 5.85-5.75 (m, $^1$H), 5.43 (dd, J=8.7 Hz, 3.6 Hz, $^1$H), 5.06-4.95 (m, 2H), 4.69 (t, J=8.8 Hz, $^1$H), 4.29 (dd, J=8.9 Hz, 3.64 Hz, $^1$H), 3.07-3.03 (m, 2H), 2.39-2.34 (m, 2H); $^{13}$C{$^1$H} NMR (100 MHz, CDCl$_3$) δ 172.2, 153.9, 139.2, 136.7, 129.3, 128.9, 126.1, 115.8, 70.2, 57.7, 35.0, 28.2; IR (KBr) 3069, 2979, 1780, 1706, 1385, 1326, 1200, 1060 cm$^{-1}$; HRMS (EI) m/z: [M]$^+$ Calcd for C$_{14}$H$_{15}$NO$_3$ 245.1052; Found 245.1051.

Step (2): Synthesis of (S)-3-((R)-2-((S)-(4-(benzyloxy)phenyl) ((4-fluorophenyl)amino)methyl)pent-4-enoyl)-4-phenyloxazolidin-2-one (Compound 5)

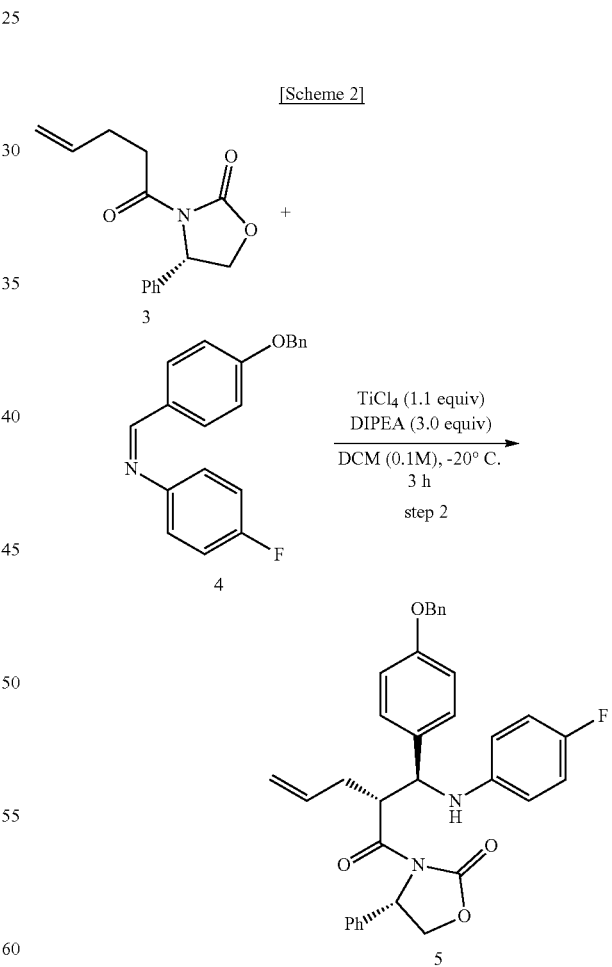

(S)-3-(pent-4-enoyl)-4-phenyloxazolidin-2-one (3, 4219 mg, 17.2 mmol) was dissolved in a DCM solvent (86 mL) and then cooled to −20° C. Subsequently, TiCl$_4$ (1 M solution in DCM) (21.9 mL, 20.6 mmol) was slowly added thereto. The resulting reaction solution was allowed to react for 15 min. After 15 min, DIPEA (5992 μL, 34.4 mmol) was slowly added thereto. The reaction was carried out for 30 min, after which a solution of (Z)-1-(4-(benzyloxy)phenyl)-N-(4-fluorophenyl)methaneimine (4, 7878 mg, 25.8 mmol) dissolved in DCM (168 mL) was slowly added thereto. The reaction was carried out at −20° C. for 2 hr. Subsequently, AcOH (acetic acid) (5.7 mL, 0.33 mL/mmol) was diluted with DCM (17.2 mL, 1 mL/mmol) and then added to the reaction solution, followed by reaction for 30 min. The temperature was elevated to room temperature, a 1 M $H_2SO_4$ aqueous solution (224 mL, 13 mL/mmol) was added thereto, and the reaction was further carried out for 30 min. The reaction was worked-up using a $NaHCO_3$ aqueous solution (600 mL) and ethyl acetate (400 mL, 133 mL×3). The ethyl acetate layer was dried with anhydrous $MgSO_4$ and then filtered. Further, recrystallization was performed using a MeOH/DCM (9/1) solvent. The obtained solid was filtered using MeOH, thus yielding a desired compound (S)-3-((R)-2-((S)-(4-(benzyloxy)phenyl) ((4-fluorophenyl)amino)methyl)pent-4-enoyl)-4-phenyloxazolidin-2-one (5, 4735 mg, 50%) (FIGS. 4 to 6).

(S)-3-((R)-2-((S)-(4-(benzyloxy)phenyl) ((4-fluorophenyl)amino)methyl)pent-4-enoyl)-4-phenyloxazolidin-2-one (5)

4735 mg, 50%, White solid; $^1H$ NMR (400 MHz, $CDCl_3$) δ 7.44-7.33 (m, 5H), 7.18-7.14 (m, 3H), 7.08-7.05 (m, 4H), 6.89-6.86 (m, 2H), 6.77-6.72 (m, 2H), 6.41-6.38 (m, 2H), 5.76-5.66 (m, $^1H$), 5.41 (dd, J=8.5 Hz, 3.1 Hz, $^1H$), 5.03-4.98 (m, 5H), 4.67-4.56 (m, 2H), 4.41-4.37 (m, $^1H$), 4.18 (dd, J=8.7 Hz, 3.1 Hz, $^1H$), 2.49-2.41 (m, $^1H$), 2.12-2.06 (m, $^1H$); $^{13}C\{^1H\}$ NMR (100 MHz, $CDCl_3$) δ 174.7, 158.3, 156.0 (J=234.9 Hz), 154.5, 143.0 (J=2.1 Hz), 138.5, 137.1, 134.9, 133.1, 129.1, 128.7, 128.4, 128.2, 128.2, 127.7, 125.4, 117.7, 115.6 (J=22.3 Hz), 115.13, 115.07, 115.0, 70.2, 60.9, 58.1, 48.5, 34.9; $^{19}F$ NMR (376 MHz, $CDCl_3$) δ −127.70; IR (KBr) 3064, 2918, 1772, 1704, 1509, 1385, 1200 $cm^{-1}$; HRMS (EI) m/z: $[M]^+$ Calcd for $C_{34}H_{31}FN_2O_4$ 550.2268; Found 550.2266.

Step (3): Synthesis of (3R,4S)-3-allyl-4-(4-(benzyloxy)phenyl)-1-(4-fluorophenyl) azetidin-2-one (Compound 6)

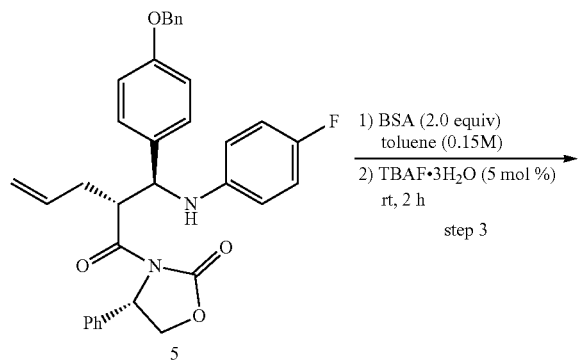

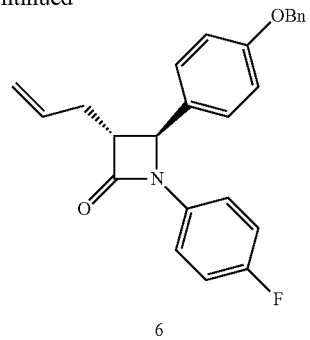

(S)-3-((R)-2-((S)-(4-(benzyloxy)phenyl) ((4-fluorophenyl)amino)methyl)pent-4-enoyl)-4-phenyloxazolidin-2-one (5, 4735 mg, 8.6 mmol) was added to a toluene solvent (86 mL) and then stirred at room temperature for 15 min (so as to maximally prevent agglomeration of Compound 5). Further, BSA (3.99 mL, 17.2 mmol) was added thereto and then the reaction was carried out at room temperature for 30 min. After 30 min, TBAF (tetrabutylammonium fluoride)-$3H_2O$ (135.7 mg, 0.43 mmol) was added thereto. After 20 to 30 min, when the reaction solution became homogeneous, the reaction was terminated by the addition of AcOH (310 μL) diluted with MeOH (45 mL). The reaction solution was treated using an evaporator to remove the solvent therefrom, after which the reaction was worked-up using a $NaHCO_3$ aqueous solution (60 mL) and ethyl acetate (60 mL, 20 mL×3). The ethyl acetate layer was dried with anhydrous $MgSO_4$ and then filtered, followed by column chromatography (ethyl acetate:hexane=1:10), thus yielding a desired compound (3R,4S)-3-allyl-4-(4-(benzyloxy)phenyl)-1-(4-fluorophenyl)azetidin-2-one (6, 3033 mg, 91%) (FIGS. 7 to 9).

(3R,4S)-3-allyl-4-(4-(benzyloxy)phenyl)-1-(4-fluorophenyl)azetidin-2-one (6)

3033 mg, 91%, White solid; Rf=0.2 (ethyl acetate:hexane=1:2); $^1H$ NMR (400 MHz, $CDCl_3$) δ 7.43-7.33 (m, 5H), 7.26-7.23 (m, 4H), 6.98-6.91 (m, 4H), 5.91-5.81 (m, $^1H$), 5.18-5.11 (m, 2H), 5.05 (s, 2H), 4.62 (d, J=2.3 Hz, $^1H$), 3.20-3.16 (m, $^1H$), 2.73-2.67 (m, $^1H$), 2.59-2.51 (m, $^1H$); $^{13}C\{^1H\}$ NMR (100 MHz, $CDCl_3$) δ 167.1, 159.2, 159.1 (J=243.0 Hz), 136.9, 134.2 134.1 (J=2.5 Hz), 129.8, 128.8, 128.3, 127.6, 127.5, 118.6 (J=7.9 Hz), 117.8, 115.9 (J=22.7 Hz), 115.6, 70.3, 60.5, 59.7, 32.9; $^{19}F$ NMR (376 MHz, $CDCl_3$) δ −118.23; IR (KBr) 3034, 2916, 1748, 1639, 1509, 1382, 1226, 1145 $cm^{-1}$; HRMS (EI) m/z: $[M]^+$ Calcd for $C_{25}H_{22}FNO_2$ 387.1635; Found 387.1634.

Step (4): Synthesis of (3R,4S)-4-(4-(benzyloxy) phenyl)-1-(4-fluorophenyl)-3-((E)-3-(4-fluorophenyl)allyl)azetidin-2-one (Compound 8)

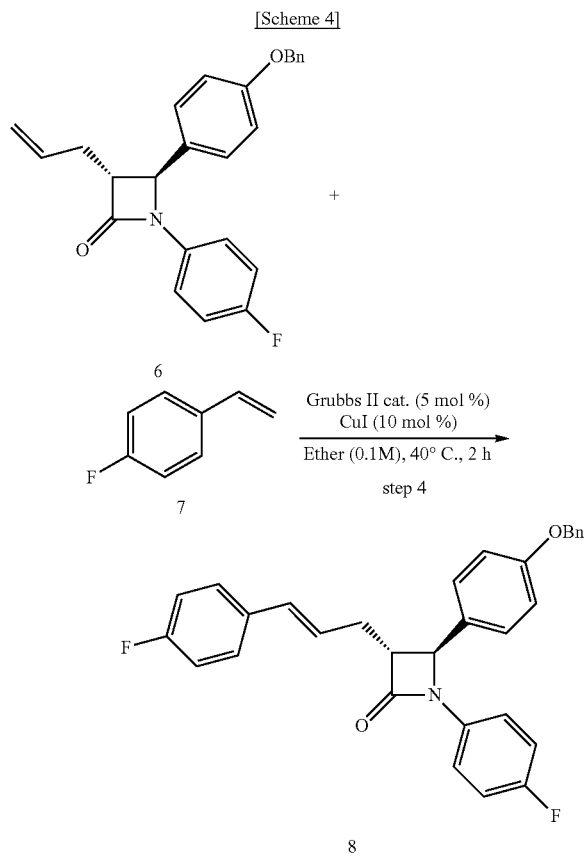

(3R,4S)-3-allyl-4-(4-(benzyloxy)phenyl)-1-(4-fluorophenyl)azetidin-2-one (6, 58.12 mg, 0.15 mmol), 1-fluoro-4-vinylbenzene (7, 179 μL, 1.5 mmol), a Grubbs $2^{nd}$ catalyst (6.37 mg, 0.0075 mmol) and CuI (2.86 mg, 0.015 mmol) were added to an ether solvent (1.5 mL) and then reacted at 40° C. for 1 hr. The reaction solution was cooled to room temperature and then filtered through silica gel using ethyl acetate, followed by column chromatography (ethyl acetate: hexane=1:10), thus yielding a desired compound (3R,4S)-4-(4-(benzyloxy)phenyl)-1-(4-fluorophenyl)-3-((E)-3-(4-fluorophenyl)allyl)azetidin-2-one (8, 50.56 mg, 70%) (FIGS. 10 to 12).

(3R,4S)-4-(4-(benzyloxy)phenyl)-1-(4-fluorophenyl)-3-((E)-3-(4-fluorophenyl)allyl)azetidin-2-one (8)

50.56 mg, 70%, White solid; Rf=0.2 (ethyl acetate: hexane=1:5); $^1$H NMR (400 MHz, CDCl$_3$) δ 7.43-7.35 (m, 5H), 7.28-7.22 (m, 6H), 7.01-6.90 (m, 6H), 7.01-6.93 (m, 4H), 6.44 (d, J=15.9 Hz, 1H), 6.18-6.11 (m, 1H), 5.04 (s, 2H), 4.66 (d, J=2.3 Hz, 1H), 3.28-3.24 (m, 1H), 2.89-2.82 (m, 1H), 2.74-2.66 (m, 1H); $^{13}$C{$^1$H} NMR (100 MHz, CDCl$_3$) δ 166.9, 162.4 (J=246.7 Hz), 159.2, 159.1 (J=243.3 Hz), 136.8, 134.1 (J=2.7 Hz), 133.2 (J=3.2 Hz), 131.5, 129.8, 128.8, 128.2, 127.8 (J=7.9 Hz), 127.6, 127.4, 125.5 (J=2.0 Hz), 118.6 (J=7.8 Hz), 115.9 (J=22.7 Hz), 115.7 (J=2.6 Hz), 115.5, 70.3, 60.6, 60.0, 32.1; $^{19}$F NMR (376 MHz, CDCl$_3$) δ -114.64, -118.08; IR (KBr) 3034, 2917, 1748, 1610, 1509, 1385, 1227, 1175, 1157, 1139 cm$^{-1}$; HRMS (EI) m/z: [M]$^+$ Calcd for C$_{31}$H$_{25}$F$_2$NO$_2$ 481.1853; Found 481.1855.

Step (5): Synthesis of (3R,4S)-4-(4-(benzyloxy) phenyl)-1-(4-fluorophenyl)-3-(3-(4-fluorophenyl)-3-oxopropyl)azetidin-2-one (Compound 9)

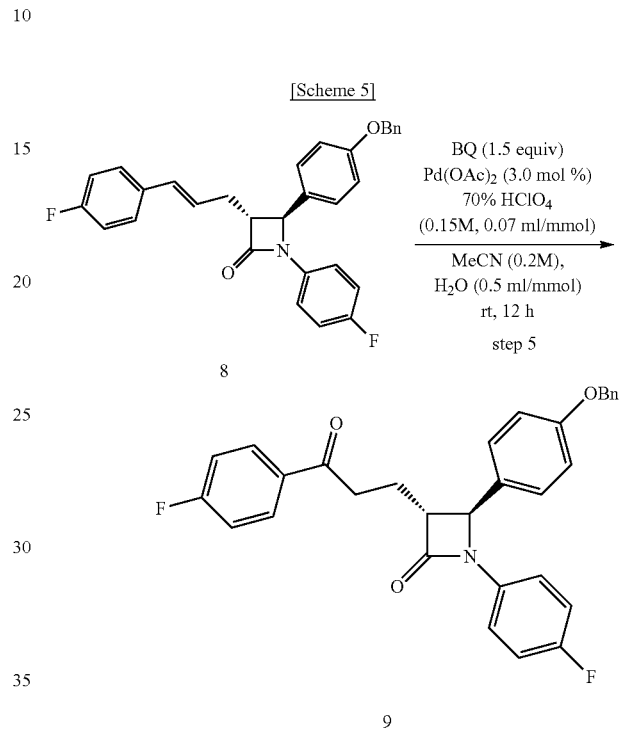

Pd(OAc)$_2$ (3.37 mg, 0.015 mmol), benzoquinone (81.07 mg, 0.75 mmol) and 70% HClO$_4$ (0.15 M aqueous solution) (35 μL, 70 μL/mmol) were added to an acetonitrile solvent (1.25 mL), and then deoxygenated with stirring for 30 min. Subsequently, H$_2$O (0.25 mL, 0.5 mL/mmol) was added thereto, followed by deoxygenation with vigorous stirring for 30 min. Subsequently, (3R,4S)-4-(4-(benzyloxy)phenyl)-1-(4-fluorophenyl)-3-((E)-3-(4-fluorophenyl)allyl)azetidin-2-one (8, 240.8 mg, 0.5 mmol) dissolved in acetonitrile (1.25 mL) was added dropwise thereto. The reaction was carried out for 4 hr, after which 70% HClO$_4$ (0.15 M aqueous solution) (35 μL) was further added thereto, and the reaction was then carried out for 12 hr. After completion of the reaction, the reaction was terminated with H$_2$O (30 mL) and extraction was performed using ethyl acetate (15 mL, 5 mL×3). The ethyl acetate layer was dried with anhydrous MgSO$_4$ and then filtered, followed by column chromatography (ethyl acetate:hexane=1:5), thus yielding a desired compound (3R,4S)-4-(4-(benzyloxy)phenyl)-1-(4-fluorophenyl)-3-(3-(4-fluorophenyl)-3-oxopropyl)azetidin-2-one (9, 223.9 mg, 90%) (FIGS. 13 to 15).

(3R,4S)-4-(4-(benzyloxy)phenyl)-1-(4-fluorophenyl)-3-(3-(4-fluorophenyl)-3-oxopropyl) azetidin-2-one (9)

223.9 mg, 90%, White solid; Rf=0.2 (ethyl acetate: hexane=1:5); $^1$H NMR (400 MHz, CDCl$_3$) δ 8.00-7.97 (m, 2H), 7.42-7.33 (m, 5H), 7.26-7.23 (m, 4H), 7.12 (t, J=8.6

Hz, 2H), 6.97-6.91 (m, 4H), 5.04 (s, 2H), 4.67 (d, J=2.1 Hz, 1H), 3.33-3.25 (m, 1H), 3.19-3.11 (m, 2H), 2.44-2.35 (m, 1H), 2.31-2.22 (m, 1H); $^{13}C\{^{1}H\}$ NMR (100 MHz, CDCl$_3$) δ 197.5, 167.4, 166.0 (J=254.7 Hz), 159.2, 159.1 (J=243.4 Hz), 136.8, 134.0 (J=2.6 Hz), 133.2, (J=3.0 Hz), 130.9, 129.7, 128.8, 128.2, 127.5 (J=24.8 Hz), 118.6 (J=7.9 Hz), 116.0 (J=7.3 Hz), 115.8 (J=6.5 Hz), 115.7, 70.3, 61.3, 60.0, 35.7, 23.3; $^{19}F$ NMR (376 MHz, CDCl$_3$) δ −104.93, −118.06; IR (KBr) 3064, 2922, 2851, 1745, 1684, 1598, 1509, 1386, 1228, 1156 cm$^{-1}$; HRMS (EI) m/z: [M]$^+$ Calcd for C$_{31}$H$_{25}$F$_2$NO$_3$ 497.1803; Found 497.1806.

Step (6): Synthesis of (3R,4S)-4-(4-(benzyloxy)phenyl)-1-(4-fluorophenyl)-3-((S)-3-(4-fluorophenyl)-3-hydroxypropyl) azetidin-2-one (Compound 10)

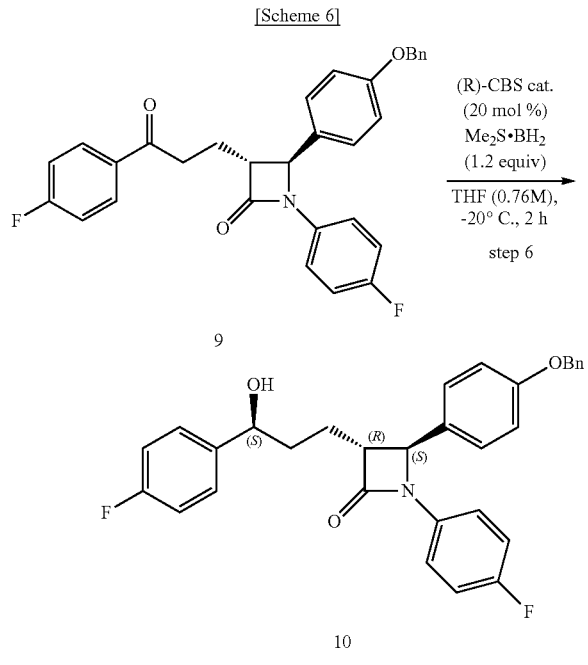

A (R)-CBS catalyst [(R)-methyl-CBS (Corey-Bakshi-Shibata) catalyst] (19.4 mg, 0.07 mmol) and (3R,4S)-4-(4-(benzyloxy)phenyl)-1-(4-fluorophenyl)-3-(3-(4-fluorophenyl)-3-oxopropyl)azetidin-2-one (9, 157.4 mg, 0.32 mmol) were dissolved in a THF (tetrahydrofuran) solvent (0.42 mL) and then stirred at −20° C. for 5 min. Subsequently, a borane dimethyl sulfide complex (Me$_2$S.BH$_3$) (2 M solution in THF) (192 μL, 0.38 mmol) was added dropwise thereto at 0.5 mL/h, after which the reaction was carried out at −20° C. for 2 hr [chiral reduction]. The reaction was terminated with MeOH (0.64 mL), and was then worked-up using a 1 M HCl aqueous solution (20 mL) and 15 mL (5 mL×3) of ethyl acetate. The extracted ethyl acetate layer was dried with anhydrous MgSO$_4$ and then filtered, followed by column chromatography (ether:hexane=1:2), thus yielding a desired compound (3R,4S)-4-(4-(benzyloxy)phenyl)-1-(4-fluorophenyl)-3-((S)-3-(4-fluorophenyl)-3-hydroxypropyl) azetidin-2-one (10, 147.1 mg, 92%) (FIGS. 16 to 18).

(3R,4S)-4-(4-(benzyloxy)phenyl)-1-(4-fluorophenyl)-3-((S)-3-(4-fluorophenyl)-3-hydroxypropyl) azetidin-2-one (10)

147.1 mg, 92%, White solid; Rf=0.2 (ether:hexane=1:2); $^1$H NMR (400 MHz, CDCl$_3$) δ 7.42-7.33 (m, 5H), 7.30-7.21 (m, 6H), 7.02-6.90 (m, 6H), 5.0 (s, 2H), 4.71-4.70 (m, 1H), 4.57 (d, J=2.0 Hz, 1H), 3.08-3.05 (m, 1H), 2.33 (s, 1H), 1.99-1.86 (m, 4H); $^{13}C\{^1H\}$ NMR (100 MHz, CDCl$_3$) δ 167.8, 162.3 (J=245.5 Hz), 159.2, 159.1 (J=243.5 Hz), 140.2 (J=3.1 Hz), 136.8, 134.0 (J=2.4 Hz), 129.8, 128.8, 128.2, 127.6, 127.5 (J=8.1 Hz), 127.3, 118.5 (J=7.9 Hz), 115.9 (J=22.7 Hz), 115.7, 115.5 (J=21.3 Hz), 73.2, 70.3, 61.2, 60.4, 36.8, 25.1; $^{19}F$ NMR (376 MHz, CDCl$_3$) δ −114.87, −118.10; IR (KBr) 3064, 3034, 2926, 2864, 1883, 1743, 1608, 1510, 1387, 1223 cm$^{-1}$; HRMS (EI) m/z: [M]$^+$ Calcd for C$_{31}$H$_{27}$F$_2$NO$_3$ 499.1959; Found 499.1960.

Step (7): Synthesis of (3R,4S)-1-(4-fluorophenyl)-3-((S)-3-(4-fluorophenyl)-3-hydroxypropyl)-4-(4-hydroxyphenyl) azetidin-2-one (Compound 11)

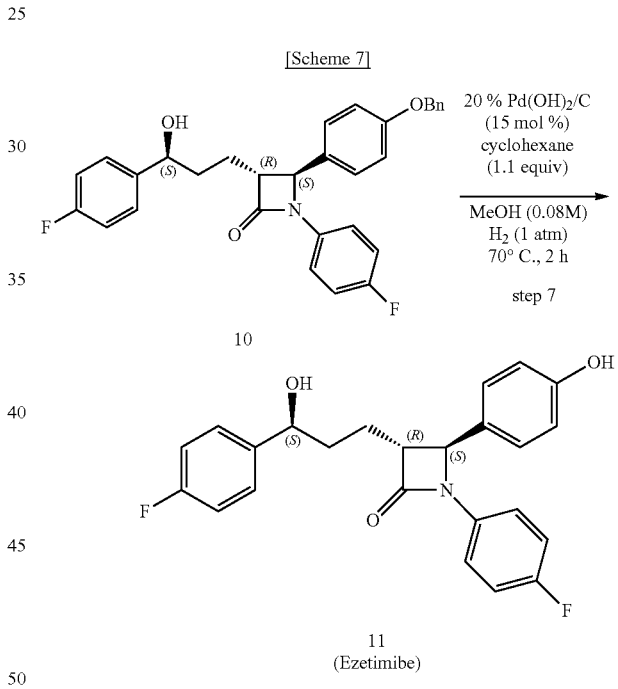

(3R,4S)-4-(4-(benzyloxy)phenyl)-1-(4-fluorophenyl)-3-((S)-3-(4-fluorophenyl)-3-hydroxypropyl) azetidin-2-one (10, 258 mg, 0.5 mmol), 20% Pd(OH)$_2$/C (10.53 mg, 15 mol %) and cyclohexane (55.71 μL, 0.55 mmol) were added to a MeOH solvent (6.25 mL) under H$_2$ (1 atm) and then reacted at 70° C. for 3 hr [deprotection]. After completion of the reaction, the reaction product was cooled to room temperature and then filtered through celite using ethyl acetate (25 mL). The filtered solution was concentrated and then recrystallized two times with MeOH and H$_2$O (1/3, 3 mL/9 mL). The obtained solid was filtered using H$_2$O (20 mL), thereby yielding a desired compound (3R,4S)-1-(4-fluorophenyl)-3-((S)-3-(4-fluorophenyl)-3-hydroxypropyl)-4-(4-hydroxyphenyl)azetidin-2-one (11, 203 mg, 99%) (FIGS. 19 to 21).

(3R,4S)-1-(4-fluorophenyl)-3-((S)-3-(4-fluorophenyl)-3-hydroxypropyl)-4-(4-hydroxyphenyl) azetidin-2-one (11)

203 mg, 99%, White solid; Rf=0.2 (ethyl acetate: hexane=1:1); 99% ee; $[\alpha]^{20}_D$ −28.05 (c 0.15, MeOH) [lit.[1] −28.1 (c 0.15, MeOH); $^1$H NMR (400 MHz, CD$_3$OD) δ 7.34-7.27 (m, 4H), 7.21 (d, J=8.5 Hz, 2H), 7.06-6.96 (m, 4H), 6.81 (d, J=8.5 Hz, 2H), 4.87 (s, 2H), 4.74 (d, J=2.0 Hz, 1H), 4.63-4.60 (m, 1H), 3.10-3.07 (m, 1H), 1.97-1.84 (m, 4H); $^{13}$C{$^1$H} NMR (100 MHz, CD$_3$OD) δ 169.9, 163.5 (J=243.6 Hz), 160.5 (J=242.0 Hz), 159.0, 142.2 (J=3.0 Hz), 135.3 (J=2.7 Hz), 129.5, 128.8 (J=8.0 Hz), 128.6, 119.9 (J=7.9 Hz), 117.0, 116.6 (J=22.9 Hz), 115.9 (J=21.6 Hz), 73.8, 62.3, 61.2, 37.5, 26.1; $^{19}$F NMR (376 MHz, CD$_3$OD) δ −117.77, −120.15; IR (KBr) 2947, 2924, 1722, 1604, 1509, 1391, 1223 cm$^{-1}$; HRMS (EI) m/z: [M]$^+$ Calcd for C$_{24}$H$_{21}$F$_2$NO$_3$ 409.1489; Found 409.1488.

Although embodiments of the present invention have been described with reference to the accompanying drawings, those skilled in the art will appreciate that the present invention may be embodied in other specific forms without changing the technical spirit or essential features thereof. Thus, the embodiments described above should be understood to be non-limiting and illustrative in every way.

The invention claimed is:

1. A method of preparing ezetimibe, which is a compound of Chemical Formula 11, comprising:
   (1) obtaining a compound of Chemical Formula 3 below by reacting a compound of Chemical Formula 1 below with a compound of Chemical Formula 2 below in the presence of DIPEA (diisopropylethylamine) and DMAP (dimethylaminopyridine);
   (2) obtaining a compound of Chemical Formula 5 below by reacting the compound of Chemical Formula 3 with a compound of Chemical Formula 4 below in the presence of TiCl$_4$ and DIPEA;
   (3) obtaining a compound of Chemical Formula 6 below by reacting the compound of Chemical Formula 5 in the presence of BSA (bis(trimethylsilyl) acetamide) and TBAF (tetrabutylammonium fluoride);
   (4) obtaining a compound of Chemical Formula 8 below by reacting the compound of Chemical Formula 6 with a compound of Chemical Formula 7 below in the presence of a Grubbs 2nd catalyst and CuI;
   (5) obtaining a compound of Chemical Formula 9 below by reacting the compound of Chemical Formula 8 in the presence of Pd(OAc)$_2$, benzoquinone and HClO$_4$;
   (6) obtaining a compound of Chemical Formula 10 below by reacting the compound of Chemical Formula 9 in the presence of a (R)-CBS (Corey-Bakshi-Shibata) catalyst and a borane dimethyl sulfide complex; and
   (7) obtaining a compound of Chemical Formula 11 below by reacting the compound of Chemical Formula 10 in the presence of palladium hydroxide on carbon and cyclohexane:

[Chemical Formula 1]

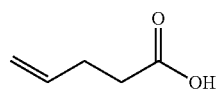

[Chemical Formula 2]

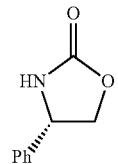

[Chemical Formula 3]

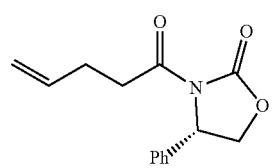

[Chemical Formula 4]

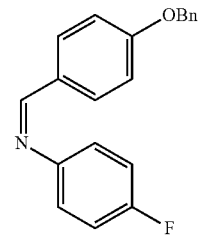

wherein Bn is benzyl,

[Chemical Formula 5]

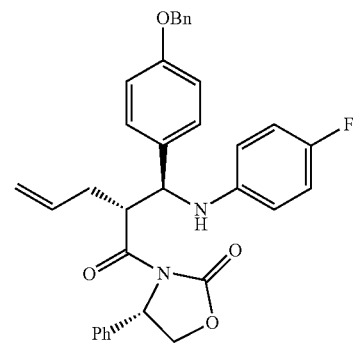

wherein Bn is benzyl,

[Chemical Formula 6]

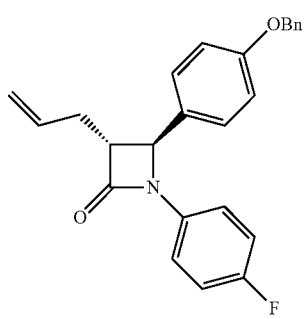

wherein Bn is benzyl,

[Chemical Formula 7]

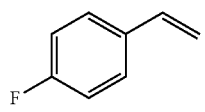

[Chemical Formula 8]

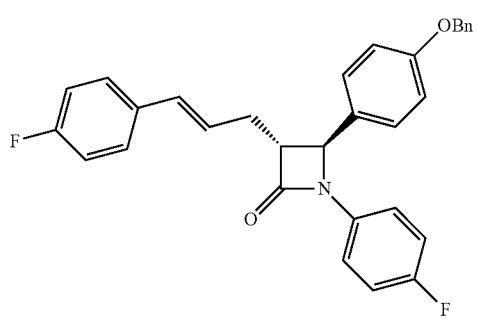

wherein Bn is benzyl,

[Chemical Formula 9]

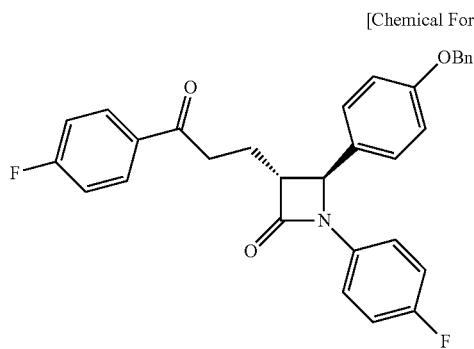

wherein Bn is benzyl,

[Chemical Formula 10]

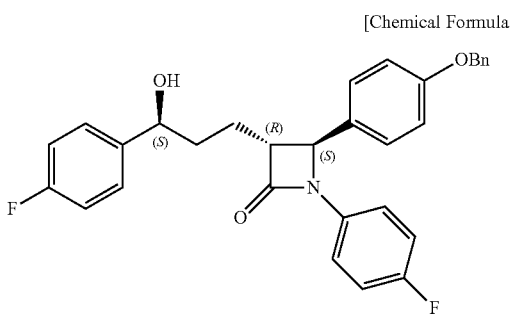

wherein Bn is benzyl,

[Chemical Formula 11]

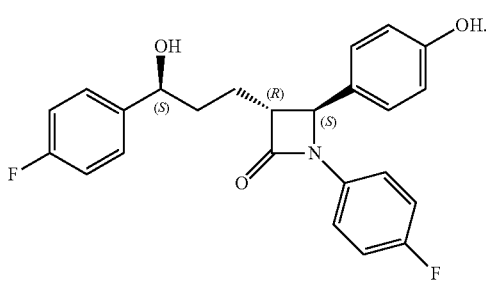

2. The method of claim 1, wherein in step (1), the DIPEA is used in an amount of 1 to 3 equivalents based on an amount of Compound 1, and the DMAP is used in an amount of 1 to 10 mol % based on the amount of Compound 1.

3. The method of claim 1, wherein in step (2), the $TiCl_4$ is used in an amount of 0.5 to 2 equivalents based on an amount of Compound 3, and the DIPEA is used in an amount of 1 to 3 equivalents based on the amount of Compound 3.

4. The method of claim 1, wherein in step (3), the BSA is used in an amount of 1 to 3 equivalents based on an amount of Compound 5, and TBAF is used in an amount of 1 to 10 mol % based on the amount of Compound 5.

5. The method of claim 1, wherein in step (4), the Grubbs $2^{nd}$ catalyst is used in an amount of 1 to 10 mol % based on an amount of Compound 7, and the CuI is used in an amount of 1 to 50 mol % based on the amount of Compound 7.

6. The method of claim 1, wherein in step (5), the benzoquinone is used in an amount of 0.5 to 5 equivalents based on an amount of Compound 8, and the $Pd(OAc)_2$ is used in an amount of 1 to 10 mol % based on the amount of Compound 8.

7. The method of claim 1, wherein in step (6), the (R)-CBS catalyst is used in an amount of 1 to 50 mol % based on an amount of Compound 9, and the borane dimethyl sulfide complex is used in an amount of 0.5 to 5 equivalents based on the amount of Compound 9.

8. The method of claim 1, wherein in step (7), the palladium hydroxide on carbon is used in an amount of 1 to 30 mol % based on an amount of Compound 10, and the cyclohexane is used in an amount of 0.5 to 5 equivalents based on the amount of Compound 10.

9. A compound of Chemical Formula 5 below:

[Chemical Formula 5]

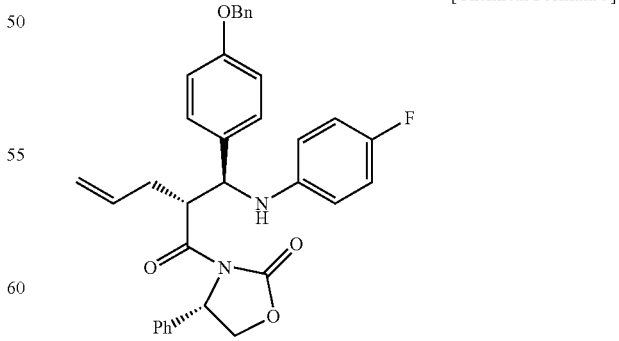

wherein Bn is benzyl.

* * * * *